(12) United States Patent
Deans et al.

(10) Patent No.: US 7,799,573 B2
(45) Date of Patent: Sep. 21, 2010

(54) DETECTION OF EXPLOSIVES AND OTHER SPECIES

(75) Inventors: Robert Deans, Grafton, MA (US);
Aimee Rose, Cambridge, MA (US);
Kevin M. Bardon, Marshfield, MA (US); Lawrence F. Hancock, North Andover, MA (US); Timothy M. Swager, Newton, MA (US)

(73) Assignee: Normadics, Inc., Stillwater, OK (US)

( * ) Notice: Subject to any disclaimer, the term of this patent is extended or adjusted under 35 U.S.C. 154(b) by 710 days.

(21) Appl. No.: 11/784,208

(22) Filed: Apr. 5, 2007

(65) Prior Publication Data
US 2008/0248578 A1  Oct. 9, 2008

Related U.S. Application Data

(63) Continuation-in-part of application No. 11/514,092, filed on Aug. 31, 2006.

(60) Provisional application No. 60/712,940, filed on Aug. 31, 2005, provisional application No. 60/918,809, filed on Mar. 19, 2007.

(51) Int. Cl.
*G01N 33/00* (2006.01)
(52) U.S. Cl. .................. 436/135; 436/127; 422/52
(58) Field of Classification Search .................. None
See application file for complete search history.

(56) References Cited

U.S. PATENT DOCUMENTS

| | | | |
|---|---|---|---|
| 3,749,679 A | 7/1973 | Rauhut | |
| 3,816,325 A | 6/1974 | Rauhut et al. | |
| 4,680,268 A | 7/1987 | Clark, Jr. | |
| 4,765,961 A | 8/1988 | Schiff et al. | |
| 5,092,220 A | 3/1992 | Rounbehler | |
| 5,348,690 A | 9/1994 | Cohen et al. | |
| 5,389,302 A | 2/1995 | Warren, Jr. | |
| 6,245,576 B1 | 6/2001 | Hiley | |

(Continued)

FOREIGN PATENT DOCUMENTS

EP  0228046 A2  7/1987

(Continued)

OTHER PUBLICATIONS

Chokshi, H. et al., "Oxalate/Hydrogen Peroxide Chemiluminescence Reaction. A $^{19}F$ NMR Probe of the Reaction Mechanism," *Biomedical Chromatography*, vol. 4, No. 3, 1990, pp. 96-99.

(Continued)

*Primary Examiner*—Yelena G Gakh
*Assistant Examiner*—David Weisz
(74) *Attorney, Agent, or Firm*—Wolf, Greenfield & Sacks, P.C.

(57) ABSTRACT

The present invention provides a series of systems, devices, and methods relating to the determination of explosives, such as peroxides or peroxide precursors, and other species. Embodiments of the invention may allow a sample suspected of containing an explosive (e.g., a peroxide) or other species to interact with a reactant, wherein the sample may react and cause light emission from the reactant. Advantages of the present invention may include the simplification of devices for determination of peroxide-based explosives, wherein the devices are portable and, in some cases, disposable. Other advantages may include relative ease of fabrication and operation.

31 Claims, 25 Drawing Sheets

U.S. PATENT DOCUMENTS

| | | | |
|---|---|---|---|
| 6,406,918 | B1 | 6/2002 | Bannister et al. |
| 6,558,626 | B1 | 5/2003 | Aker et al. |
| 6,579,722 | B1 | 6/2003 | Collins et al. |
| 6,605,693 | B1 | 8/2003 | Becker et al. |
| 6,716,637 | B2 | 4/2004 | Weckstrom |
| 6,767,717 | B1 | 7/2004 | Itzhaky et al. |
| 7,141,677 | B2 | 11/2006 | Lee et al. |
| 2004/0051867 | A1 | 3/2004 | Brestel et al. |
| 2004/0053421 | A1 | 3/2004 | Nguyen et al. |
| 2004/0114130 | A1 | 6/2004 | Nguyen et al. |
| 2004/0171098 | A1 | 9/2004 | Akhavan-Tafti et al. |
| 2006/0088441 | A1 | 4/2006 | Hill |

FOREIGN PATENT DOCUMENTS

| | | |
|---|---|---|
| EP | 0745684 A1 | 12/1996 |
| GB | 2095401 A | 9/1982 |
| WO | WO 97/47958 A1 | 12/1997 |
| WO | WO 99/57222 A1 | 11/1999 |

OTHER PUBLICATIONS

Shamispur, M. et al., "Effect of some aminoanthraquinone derivatives as red fluorescers on chemiluminescence systems originating from bis-(2,4,6-trichlorophenyl) oxalate and lucigenin," *Journal of Photochemistry and Photobiology*, vol. 172, 2005, pp. 23-27.

Stigbrand, M.et al., "1,1'-Oxalyldiimidazole as Chemiluminescence Reagent in the Determination of Low Hydrogen Peroxide Concentrations by Flow Injection Analysis," *Analytical Chemistry*, vol. 66, No. 10, 1994, pp. 1766-1770.

Yang, J., et al., "Fluorescent Porous Polymer Films as TNT Chemosensors: Electronic and Structural Effects," *J. American Chemical Society*, vol. 120, No. 46, 1998, pp. 11864-11873.

Invitation to Pay Additional Fees and Partial International Search Report for International Application No. PCT/US2007/019248, mailed on Aug. 6, 2008.

Bakaltcheva, I. et al., "A fiber optic biosensor for multianalyte detection: importance of preventing fluorophore aggregation," *Sensors and Actuators B* 1998, 51, 46.

Buttigieg, G. A. et al., "Characterization of the explosive triacetone triperoxide and detection by ion mobility spectroscopy," *Forensic Sci. Int*, 2003, 135, 53.

Crowson, A. et al., "Development of a LC/MS method for the trace analysis of hexamethyltriperoxidediamine," *Analyst* 2001, 126, 1689.

Dubnikova, F. et al., "Novel approach to the detection of triacetonetriperoxide (TATP): Its structure and its complexes with ions," *J. Phys. Chem. A* 2002, 106, 4951.

Kok, G. et al., "Chemiluminescent Method for Determination of Hydrogen Peroxide in the Ambient Atmosphere," *American Chemical Society* 1978, vol. 12, No. 9, 1072.

Oxley, J. et al., "Training Dogs to Detect Triacetone Triperoxide (TATP)," *Sensors and Command, Control, Communications, and Intelligence (C3I) Technologies for Homeland Security and Homeland Defense III*, E.M. Carapezza, ed., Proc. of SPIE 2004, vol. 5403, 349.

Robinson, J. et al., "Luminol/$H_2O_2$ Chemiluminescence Detector for the Analysis of Nitric Oxide in Exhaled Breath," *Anal. Chem*, 1999, vol. 71, No. 22, 5131.

Schulte-Ladbeck, R. et al., "A field test for the detection of peroxide-based explosives," *Analyst* 2002, 127, 1152.

Schulte-Ladbeck, R. et al., "Determination of triacetonetriperoxide in ambient air," *Anal. Chem. Acta* 2003, 482, 183.

International Search Report and Written Opinion, mailed Feb. 20, 2008, for International Application No. PCT/US07/18722.

International Search Report and Written Opinion, mailed Nov. 17, 2008, for International Application No. PCT/US07/019248.

Kietzmann, D., et al., "Hydrogen peroxide in expired breath condensate of patients with acute respiratory failure and with ARDS", Intensive Care Med (1993) 19:78-81.

Lazrus, A., et al., "Automated Fluorometric Method for Hydrogen Peroxide in Air", Anal. Chem, 1986, 58, 594-597.

FIG. 1
a.) 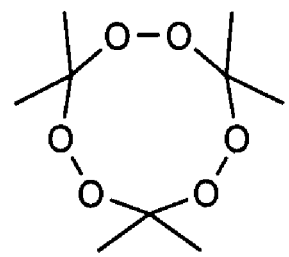
b.) 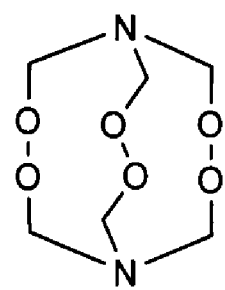

FIG. 2
a.)
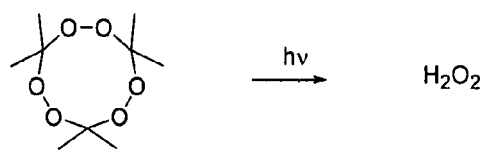
b.)
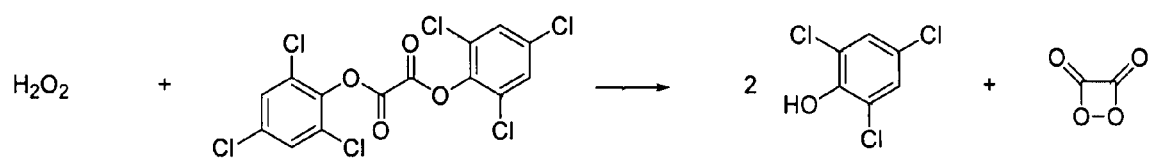
c.)
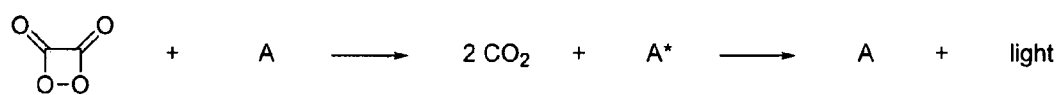

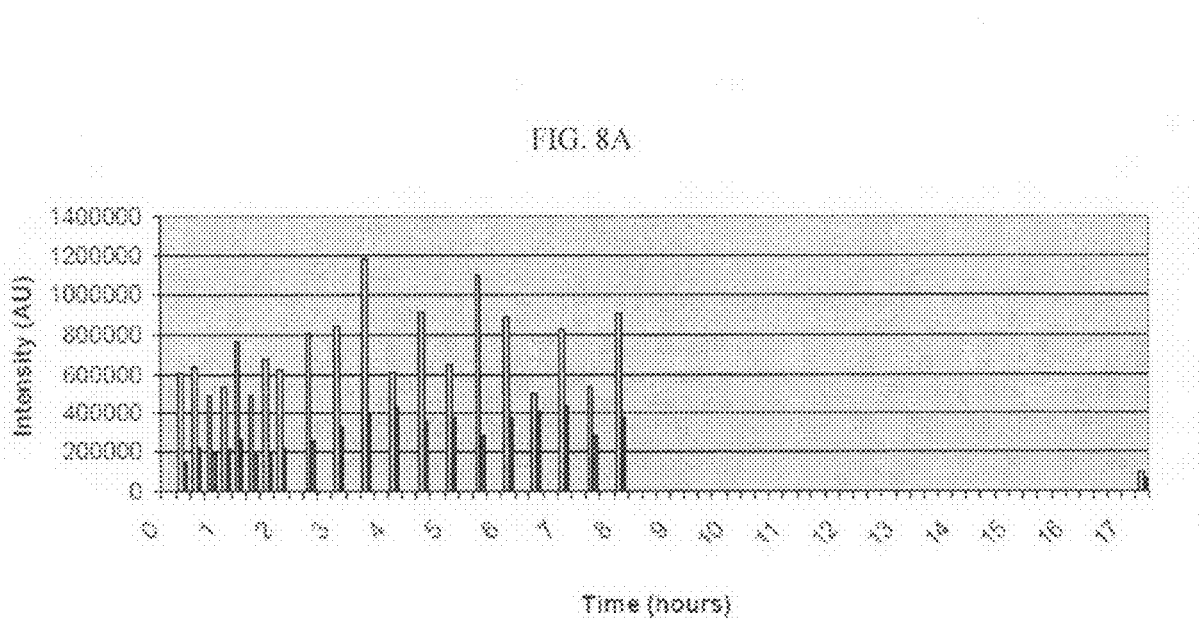

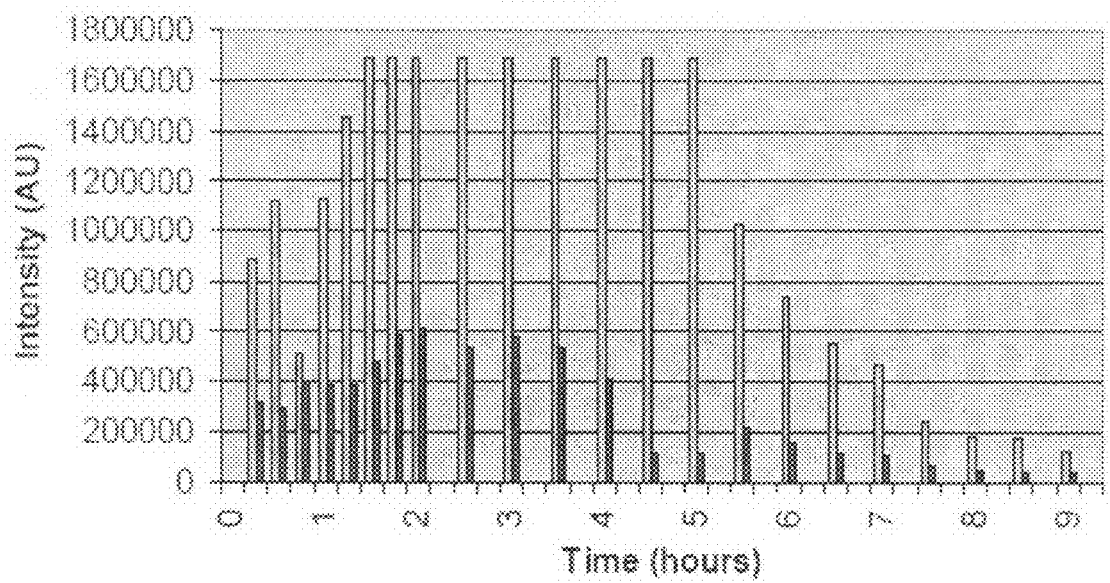
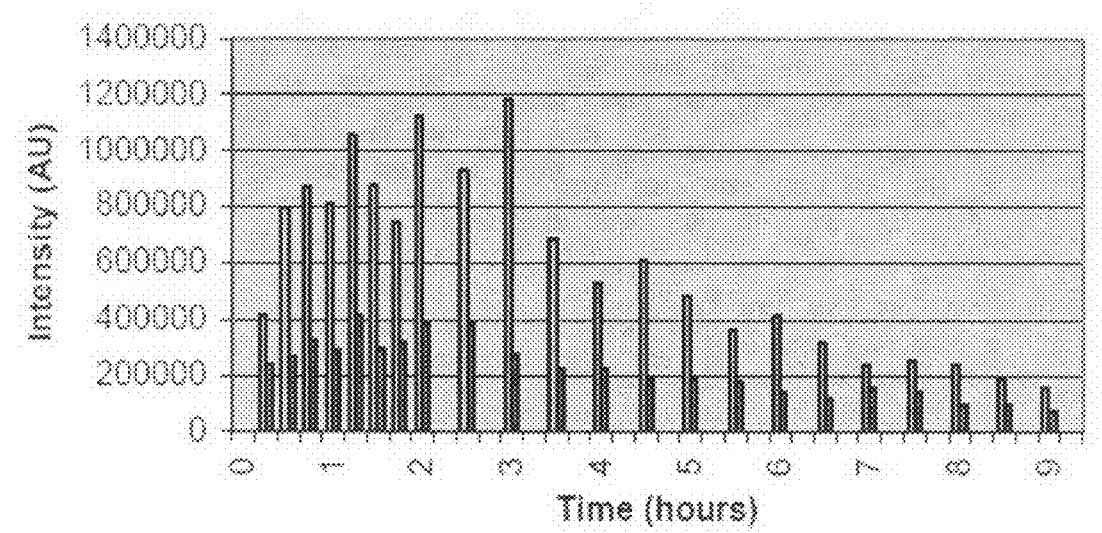

Time (hours)

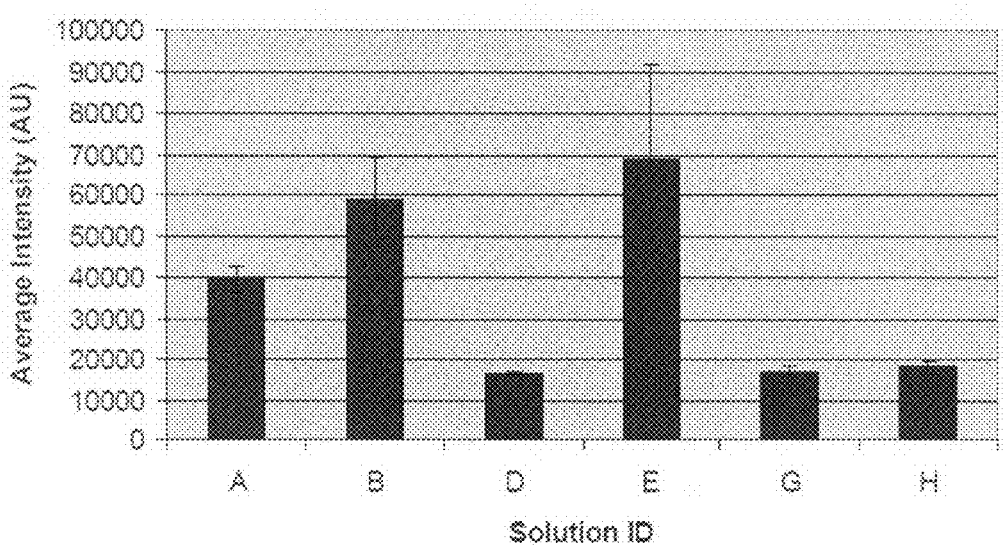
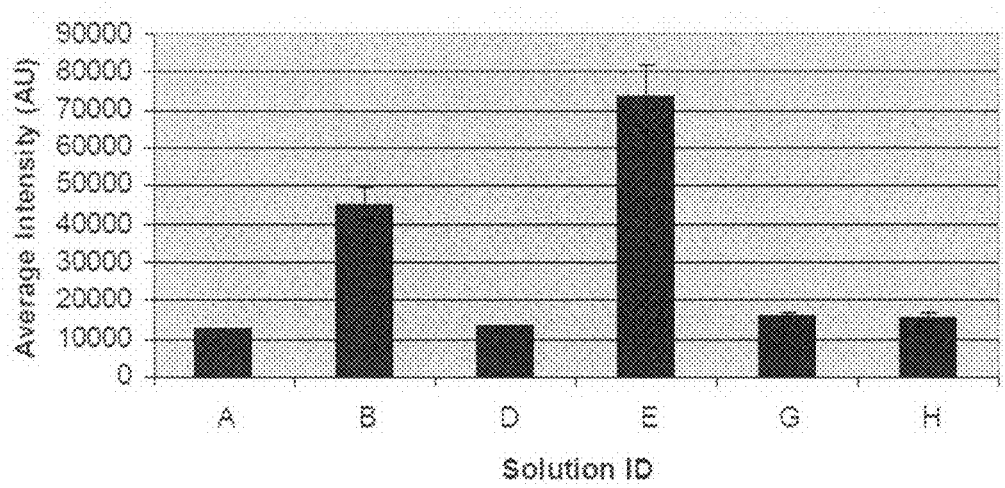

US 7,799,573 B2

DETECTION OF EXPLOSIVES AND OTHER SPECIES

RELATED APPLICATIONS

This application is a continuation-in-part of U.S. application Ser. No. 11/514,092, filed Aug. 31, 2006, which claims priority to U.S. Provisional Application No. 60/712,940, filed Aug. 31, 2005, the contents of which are incorporated herein by reference. This application also claims priority to U.S. Provisional Application Ser. No. 60/918,809, filed Mar. 19, 2007, the contents of which are incorporated herein by reference.

STATEMENT REGARDING FEDERALLY SPONSORED RESEARCH OR DEVELOPMENT

This invention was made with the support under the following government contract; HDTS04-04-G-RED943, awarded by the Transportation Security Administration. The government has certain rights in the invention.

FIELD OF THE INVENTION

The present invention relates to systems, devices, and methods for the determination of peroxides, peroxide precursors, explosives, and other species.

BACKGROUND OF THE INVENTION

The rise in terrorist activities in recent years has caused a greater demand for chemical sensor devices for detecting vapors of explosive materials. For example, peroxide-based explosives such as triacteone triperoxide (TATP) and hexamethylene triperoxide diamine (HMTD) are extremely sensitive to detonation by heat, friction, impact, and electrical discharge. Methods of manufacturing such explosives are widely known and can be carried out with relative ease and, since the starting materials needed to synthesize these materials are readily available, the use of peroxide-based explosives has become increasing popular among terrorists.

Existing methods for the vapor phase detection of such explosive materials typically require solution preparation, long sampling times, and are generally not readily field-deployable. Other methods, such as cavity ringdown spectroscopy, typically require delicate optics setup and high power lasers that are also not generally amenable to in-field use. Furthermore, devices such as these often require an external means for photodetection and signal amplification (e.g., a photomultiplier tube). Such equipment can prove costly to fabricate and operate, and can add bulk to the device. Additionally, many standard testing procedures for determining the presence of explosive compounds require excessive periods of time or lack the sensitivity necessary for in-field use.

Accordingly, improved devices and methods are needed.

SUMMARY OF THE INVENTION

The present invention relates to systems for determining a peroxide or a peroxide precursor comprising a peroxide-reactive material, a light-emitting material, a support material, and, optionally, a catalyst, wherein the support material has a boiling point of at least 300° C. or greater.

The present invention also provides methods for making compositions for determining a peroxide or a peroxide precursor, comprising forming a fluid mixture comprising a peroxide-reactive material, a light-emitting material, a support material or support material precursor, and, optionally, a catalyst, to produce a composition that is emissive in the presence of a peroxide, wherein the composition has a boiling point of at least 300° C. or greater.

The present invention also provides methods for determining a peroxide comprising exposing a composition comprising a peroxide-reactive material to a vapor suspected of containing a peroxide, wherein the peroxide, if present, causes the composition to generate a determinable signal, wherein the composition has a boiling point of at least 300° C. or greater; and determining the signal.

The present invention also provides methods for determining an explosive in an area comprising distributing a composition on a surface in an area suspected of containing an explosive; determining a chemiluminescence of the composition; and identifying the area as an area containing an explosive.

The present invention also provides methods for determination of an organic peroxide explosive comprising exposing a sensor material to a vapor suspected of containing an organic peroxide explosive, wherein the organic peroxide explosive, if present, causes the sensor material to generate a determinable signal, wherein the sensor material has a boiling point of at least 300° C. or greater; and determining the signal.

The present invention also provides methods for determination of a peroxide precursor comprising exposing a vapor suspected of containing a peroxide precursor to conditions sufficient to convert the peroxide precursor, if present, to a peroxide; exposing a composition comprising a peroxide-reactive material to the vapor, wherein the peroxide, if present, causes the composition to generate a determinable signal; and determining the signal.

The present invention also relates to devices comprising an inlet for intake of a vapor sample, a sample cell comprising a peroxide-reactive material constructed and arranged to receive the vapor sample, and a detection mechanism in optical communication with the sample cell.

The present invention also relates to devices for detection of an explosive comprising an inlet for intake of a vapor sample, a sample cell comprising a material reactive with an explosive or a reactant or a decomposition product of the explosive, the sample cell constructed and arranged to receive the vapor sample; and a detection mechanism in optical communication with the sample cell, wherein the detection mechanism is free of an excitation source.

BRIEF DESCRIPTION OF THE DRAWINGS

FIG. 1 illustrates examples of peroxide-based explosives, (a) triacteone triperoxide (TATP) and (b) hexamethylene triperoxide diamine (HMTD).

FIG. 2 shows an illustrative system of the invention.

FIG. 11 shows the average luminescence intensity response for chemiluminescent formulations placed in (a) frosted capillaries and (b) frosted capillaries with frosted beads, upon exposure to peroxide vapor.

DETAILED DESCRIPTION

Figure 3:
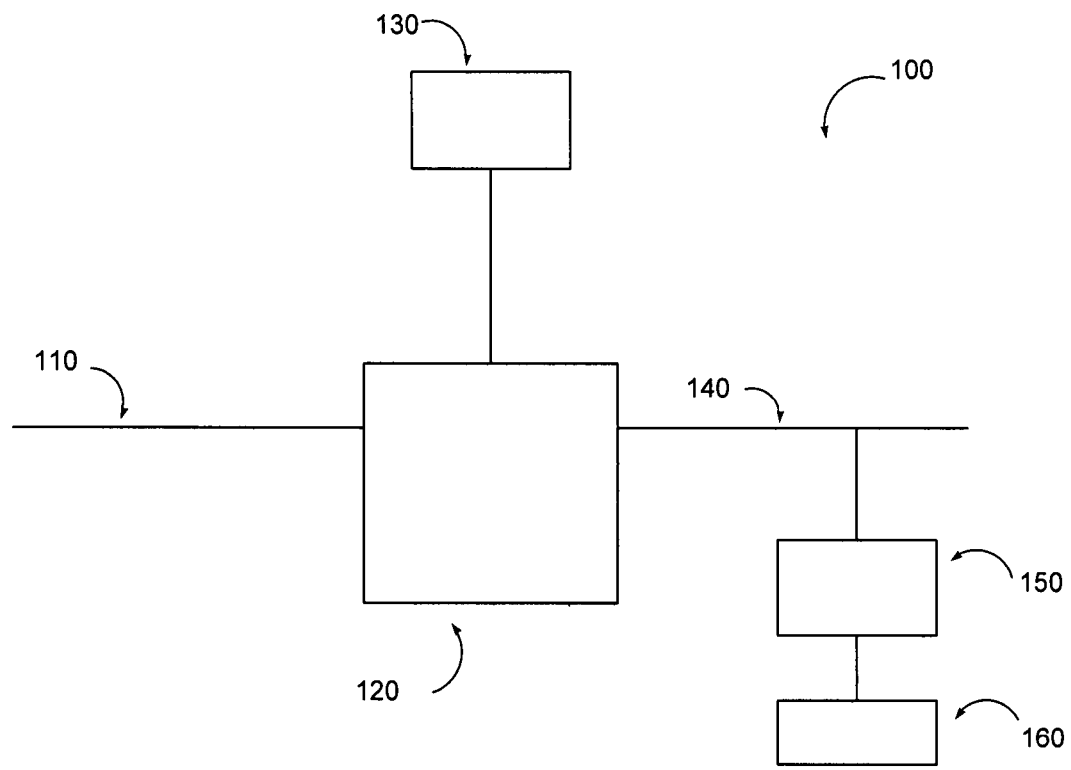
FIG. 3 illustrates, schematically, a system for determining an explosive according to one embodiment of the invention.

The present invention provides a series of systems, devices, and methods relating to the determination of explosives, such as peroxides or peroxide precursors, and other species.

For example, one relatively simple system of the invention allows the user to expose a sample suspected of containing a peroxide (e.g., a peroxide resulting from breakdown of an explosive composition) to an input of a device which moves the sample, via a gas passageway, to a reaction region containing a reactant, where any peroxide in the sample reacts and causes light emission without the need for an excitation source. In some cases, this may allow for fabrication of small, lightweight, portable, hand-held detectors that may be useful in many applications, including security systems, such as airport security systems, for example.

In one set of embodiments, systems of the present invention comprise peroxide-reactive materials which may interact with a vapor comprising a peroxide (or peroxide precursor) to generate a determinable signal. In some embodiments, the signal is a chemiluminescence of the system. Systems of the present invention may also include components which are capable of activating a peroxide precursor to generate a peroxide, wherein the peroxide reacts with the peroxide-reactive materials and causes light emission without the need for an excitation source. Advantages of the present invention may include the simplification of devices for determination of peroxide-based explosives, wherein the devices are portable and, in some cases, disposable. Other advantages may include relative ease of fabrication and operation.

One aspect of the present invention provides systems for the determination of peroxides or peroxide precursors, such as organic peroxide explosives. In some cases, the peroxide precursor may be triacteone triperoxide (TATP), hexamethylene triperoxide diamine (HMTD), or mixtures thereof. As used herein, the term "determination" refers to quantitative or qualitative analysis of a species via, for example, sight, spectroscopy, ellipsometry, piezoelectric measurement, immunoassay, electrochemical measurement, and the like. Systems of the invention may comprise a peroxide-reactive material, a light-emitting material, and a support material, wherein the system may be in either solid or liquid form. In some embodiments, the peroxide-reactive material may interact (e.g, undergo a chemical reaction) with a peroxide molecule, which may either directly generate an observable signal (e.g., light emission) or may initiate a series of chemical reactions which may lead to the generation of the observable signal. The light-emitting material may, in connection with the interaction of the peroxide-reactive material with a peroxide or peroxide precursor, give rise to the observable signal. Systems of the invention may also optionally comprise a catalyst.

Systems of the invention may be provided in any form, including liquid, solid, gel, and the like. In some cases, the system may be a liquid (e.g., solution, dispersion, emulsion, etc.) In some cases, the system may be a solid. In some embodiments, each of the peroxide-reactive material, light-emitting material, support material, and catalyst, if present, is in solid form. In some embodiments, each of the peroxide-reactive material, light-emitting, support material, and catalyst, if present, is in liquid form. In some embodiments, each of the peroxide-reactive material, light-emitting material, and catalyst, if present, are supported on the support material. In some embodiments, the peroxide-reactive material, light-emitting material, and catalyst, if present, are combined in a homogenous mixture and the mixture is supported on the support material. In some embodiments, the peroxide-reactive material and the light-emitting material, and catalyst, if present, may be evenly dispersed throughout the support material. In some embodiments, the peroxide-reactive material and the light-emitting material, and catalyst, if present, may be impregnated within the support material. In some embodiments, the peroxide-reactive material and the light-emitting material, and catalyst, if present, may be adsorbed onto the support material. In some embodiments, when combined, the peroxide-reactive material, light-emitting material, the support material, and catalyst, if present, form a solution.

Systems of the invention may also be selected or designed to exhibit a low or negligible vapor pressure and/or a boiling point of at least 300° C. or greater. For example, the system may be in liquid form, wherein the system has a low or negligible vapor pressure. In some cases, at least one component of the system (e.g., the support material) can be a material having a boiling point at least 300° C. or greater. Examples of such materials include liquids such as dicyclohexyl phthalate and dioctyl terephthalate, and ionic liquids. Systems having low or negligible vapor pressure and/or a high boiling point may be advantageous in reducing or preventing, for example, solvent evaporation, leakage, device contamination, undesirable changes in the optical properties, selectivity, and/or sensitivity of the system, or other disadvantages arising due to use of materials having greater volatility. For example, damage to certain components of the devices (e.g., optics, detectors, pump, seals, O-rings, etc.) due to condensation of volatile materials may be reduced. Some embodiments of the invention may also exhibit enhanced performance (e.g., increased reaction rates) when using a liquid-phase system. The use of systems having low volatility may also facilitate air flow, vapor phase sampling, and vapor phase detecting within devices and methods as described herein. Furthermore, the device configuration and design may be simplified.

Systems of the present invention may also include one or more components which may be capable of activating a peroxide precursor (e.g., an organic peroxide explosive) to generate a peroxide molecule or peroxide-containing species, which may then interact with the peroxide-reactive material as described herein. The component may be a source of energy which, when applied to the peroxide precursor, is capable of converting the peroxide precursor to a peroxide molecule, such as hydrogen peroxide, for example, or other peroxide-containing species. The source of energy may be thermal, electric, magnetic, optical, acoustic, electromagnetic, mechanical or the like. In some cases, the source of energy may be electromagnetic radiation, such as ultraviolet light or visible light. In some embodiments, the electromagnetic radiation has a wave length of 350 nm or less, or, more preferably, 254 nm or less, or 200 nm or less. In some cases the source of energy may also be thermal energy, wherein the peroxide precursor is exposed to a temperature sufficient to convert the peroxide precursor to a peroxide molecule or peroxide-containing species.

In some embodiments, the systems of the invention may also comprise a component capable of converting a peroxide precursor to a peroxide molecule or peroxide-containing species. The component may be a chemical species, such as an acid, wherein exposure of the peroxide precursor to the acid results in the conversion of the peroxide precursor to a peroxide molecule or peroxide-containing species. Examples of acids suitable for use in the invention include, but are not limited to, sulfuric acid, hydrochloric acid, acetic acid, and the like. In some cases, the acid may be sulfuric acid. Those of ordinary skill in the art would be able to select appropriate acids (e.g., acids having a pH less than 7) for use in the invention.

The system may optionally include other components which may enhance the stability and/or performance of the system. In some embodiments, the system further comprises a catalyst which facilitates the interaction of the peroxide-reactive material with the peroxide (or peroxide precursor) molecule. The catalyst may enhance the performance of the system, resulting in faster generation of signal, increased signal, etc. In some embodiments, the system further comprises an acid, base, or buffer. For example, in some embodiments, it may desired that the mixture have a pH greater than 7 to avoid undesirable reactions in the presence of acid. In some embodiments, the system further comprises a material capable of converting a peroxide precursor to a peroxide. For example, the material may comprise an acid, which may facilitate, for example, degradation of TATP to hydrogen peroxide.

In one embodiment, the present invention provides devices which may comprise an inlet for intake of a vapor sample, a sample cell comprising the peroxide-reactive material, catalyst, and light-emitting material, the sample cell constructed and arranged to receive the vapor sample, and a detection mechanism in optical communication with the sample cell. Systems such as this may be useful in the determination of, for example, peroxides and peroxide precursors. As used herein, a sample cell "constructed and arranged" refers to a sample cell provided in a manner to direct the passage of a vapor sample, such as a vapor comprising a peroxide, from the inlet into the sample cell, such that the vapor sample contacts at least the peroxide-reactive material. "Optical communication" may refer to the ability of the detection mechanism to receive and detect an optical signal (e.g., light emission) from the sample cell.

Systems of the invention may further include a component which may reduce any background signal caused by, for example, excess hydrogen peroxide vapor in a sample (e.g., hydrogen peroxide which has not been generated by a target analyte (e.g., such as a peroxide precursor or organic explosive peroxide). For example, systems of the invention may further comprise an absorbent material for hydrogen peroxide. The system may be constructed and arranged such that a vapor sample comprising both an organic peroxide explosive and excess hydrogen peroxide vapor may be exposed to the absorbent material prior to exposure to a source of energy, acid, and/or the sample cell comprising the peroxide-reactive material as described herein. The absorbent material may reduce the amount of excess hydrogen peroxide vapor from the sample (e.g., "clean" or "scrub" the sample). Upon exposure of the "cleaned" sample to a source of energy or an acid as described herein, the organic peroxide explosive, if present, may then be converted to a peroxide molecule. This "cleaning" process may enhance the selectivity of systems of the invention. Absorbent materials capable of absorbing hydrogen peroxide are known in the art and include various polymeric materials, such as butyl rubber.

Methods for synthesizing systems for determining a peroxide or a peroxide precursor may comprise forming a fluid mixture comprising a peroxide-reactive material, a light-emitting material, a support material or support material precursor, and, optionally, a catalyst, to produce a composition (e.g., system) that is emissive in the presence of a peroxide. The compositions may be in liquid, solid, or gel form, for example. In certain cases, forming the fluid mixture may comprise providing the support material precursor as a fluid, and dissolving or suspending the peroxide-reactive material, light-emitting material, and catalyst, if present, in the fluid support material precursor. In some embodiments, forming the fluid mixture may comprise providing the support material as a solid, and suspending (i.e., immersing) the support material in the fluid mixture.

In a particular embodiment, forming the fluid mixture may comprise dissolving or suspending the peroxide-reactive material, light-emitting material, and support material or support material precursor in an auxiliary fluid. In some embodiments, the auxiliary fluid is a solvent, such that forming the fluid mixture comprises dissolving the peroxide-reactive material, light-emitting material, and support material or support material precursor in the solvent. Optionally, a catalyst, acid, base, buffer, and/or other additives (e.g., plasticizers, preservatives, antioxidants, radical scavengers such as BHT, etc.) may be added to the fluid mixture. In some cases, the fluid mixture may form a liquid composition. In some cases, the fluid mixture may be treated (e.g., solidified) to form a solid composition. Solidification of the fluid mixture may comprise, in cases where a solvent is employed as an auxiliary fluid, removal of a solvent by, for example, evaporation or filtration. For example, the fluid mixture may be spin-cast to form a film or coating on a substrate. Solidification of the fluid mixture may also comprise, in cases where the support material precursor is provided as a fluid, conversion of the support material precursor to a support material (e.g., a solid support material).

In some embodiments, methods for synthesizing systems for determining a peroxide or a peroxide precursor as described herein may produce emissive compositions which are chemiluminescent. In one embodiment, the resulting system is a liquid. In one embodiment, the resulting system is a powder. In some embodiments, the system may have a shape or be formed into a shape (for example, by casting, molding, extruding, and the like). In some embodiments, the support material may be a film, a bottle, a sphere, a tube, a strip such as an elongated strip or tape, or the like.

Another aspect of the present invention provides methods for the determination of a peroxide or peroxide precursor. As used herein, a "peroxide precursor" may be a material which may generate a peroxide upon activation, for example, by electromagnetic radiation or an acid. Such methods may comprise exposing a composition comprising a peroxide-reactive material (e.g., according to systems described herein) to a vapor suspected of containing a peroxide, wherein the peroxide, if present, causes the composition to generate a determinable signal (e.g., a light emission), and determining the signal.

In some embodiments, the peroxide or peroxide precursor may be an organic peroxide explosive. As used herein, an "organic peroxide explosive" includes organic materials comprising one or more peroxide moieties (e.g., —O—O—), as well as any organic material that may be treated or otherwise activated to produce a species containing a peroxide moiety, that may be used as an explosive. In some embodiments, the vapor may comprise peroxide-based explosives (e.g., organic peroxide explosives) such as TATP and HMTD, as shown in FIG. 1. In some cases, TATP may be "activated" or degraded into hydrogen peroxide vapor by exposure to electromagnetic radiation (e.g., ultraviolet light, 254 nm light, etc.) or by exposure to acid to generate hydrogen peroxide vapor, which may then be determined by systems described herein.

Other examples of peroxides and/or peroxide precursors include hydrogen peroxide, urea hydrogen peroxide, sodium pyrophosphate peroxide, histidine peroxide, sodium perborate, and the like.

The present invention also provides methods for determination of an organic peroxide explosive, wherein the method comprises exposure of a sensor material (e.g., system, as described herein) to a vapor suspected of containing an organic peroxide explosive. If present, the organic peroxide explosive may cause the sensor material to generate a determinable signal, wherein determination of the signal may determine the organic peroxide explosive. In some cases, the sensor material may comprise a peroxide-reactive material, light-emitting material, support material, and/or other components as described herein (e.g., catalyst). In some cases, the method may comprise exposure of the vapor sample to a source of energy wherein the organic peroxide explosive, if present, may be converted to hydrogen peroxide, which, if present, may react with the peroxide-reactive material and cause the sensor material to generate the determinable signal.

In some embodiments, the method may comprise exposure of the vapor sample to an acid, wherein the organic peroxide explosive, if present, may be converted to hydrogen peroxide which, if present, may react with the peroxide-reactive material and cause the sensor material to generate a determinable signal.

The present invention may also comprise methods for determination of peroxide precursor, wherein the method comprises exposing a vapor suspected of containing a peroxide precursor to conditions sufficient to convert the peroxide precursor, if present, to a peroxide species. In some cases, the conditions may comprise exposure to a source of energy, such as electromagnetic radiation. In some cases, the conditions may comprise exposure to an acid. Subsequent exposure of the vapor to a composition comprising a peroxide-reactive material may allow the peroxide, if present, to interact with the composition to generate a determinable signal. Determination of the signal may then determine the peroxide precursor.

In some embodiments, the signal may be an emission of light. In some embodiments, the signal may be generated by chemiluminescence, fluorescence, phosphorescence, and/or combinations thereof. Some embodiments of the invention may generate a chemiluminescent signal arising from a chemiluminescent reaction occurring upon exposure of the system to a vapor comprising a peroxide (or peroxide precursor). The term "chemiluminescence" is known in the art and may refer to the emission of light resulting from a chemical reaction or series of chemical reactions. As used herein, a "chemiluminescent material" or "chemiluminescent solid" may refer to systems of the invention (e.g., peroxide-reactive systems) that have the capability to perform a chemiluminescent reaction. In some cases, a peroxide may initiate the chemiluminescent reaction. In some cases, the signal generated by the presence of the peroxide or peroxide precursor may be observable by sight.

For example, in the illustrative embodiment shown in FIG. 2, a method of the invention may comprise the use of a system comprising bis(2,4,6-trichlorophenyl)oxalate (i.e., as the peroxide-reactive material) and a light-emitting material A (such as anthracene, diphenylanthracene, or 9,10-bis(phenylethynyl)anthracene) supported by a support material, such as corn starch. As shown in FIG. 2A, TATP may be degraded to hydrogen peroxide by exposure to ultraviolet light. The resulting hydrogen peroxide may then react with bis(2,4,6-trichlorophenyl)-oxalate to form 1,2-dioxetanedione. (FIG. 2B) Because 1,2-dioxetanedione is highly strained and reactive, it quickly decomposes to $CO_2$ in a highly exothermic reaction, transferring energy to the light-emitting material A. Thus, light emission via a chemiluminescent reaction may observed from the light-emitting material A. The light emission may be observed by sight, without need for additional photodetection equipment.

In other embodiments, the system may comprise an oxalate, a light-emitting material comprising an iptycene, and a support material having a boiling point of at least 300° C. For example, the system may be a liquid chemiluminescent material comprising an oxalate (e.g., bis(2-carbopentyloxy-3,5,6-trichlorophenyl)oxalate (CPPO), oxalic acid bis[2,4,5-trichloro-6-(pentyloxycarbonyl)phenyl]ester), a light-emitting material (e.g., a material comprising anthracene covalently bonded to an iptycene), and a liquid support material (e.g., dicyclohexyl phthalate or dioctyl terephthalate). In some cases, the system may be coated onto a bead-filled capillary, as described herein.

In an illustrative embodiment, the system may comprise 49.875 weight % CPPO, 0.25 weight % iptycene-containing anthracene light-emitting material, and 49.875 weight % dicyclohexyl phthalate.

Other light-emitting processes and reactions (e.g., chemiluminescent, fluorescent, or phosphorescent processes) are known in the art and may be incorporated into the present invention. For example, in another illustrative embodiment, a system of the invention may comprise 3-amino-phthalhydrazide ("luminol") as the peroxide-reactive material, a catalyst (such as copper or iron compounds, or potassium ferricyanide, for example), and a base supported by an appropriate support material. In the presence of a peroxide or peroxide precursor, 3-amino-phthalhydrazide may be converted to an excited state aminophthalate ion, which then relaxes to its ground state through chemiluminescence, emitting a photon in the visible region of the spectrum ($\lambda$=425 nm). Those skilled in the art would readily recognize other light-emitting systems which may be incorporated within the scope of the invention.

In another aspect, the present invention also provides a method for determining an explosive in an area, comprising distributing a solid (e.g., a solid-state, chemiluminescent system as described herein) on a surface in an area suspected of containing an explosive. The chemiluminescence of the solid may be determined, thus identifying the area as an area containing an explosive. The area may be a surface of a piece of luggage, a surface of an automobile, an area of land or building where it is suspected that explosives are manufactured, stored, or the like, or any other area that might carry explosives or trace amounts of explosive residue and the user of the invention would like information as to the presence of explosives.

Another aspect of the invention provides devices for the determination (e.g., detection) of explosives. The device may be suitable as, for example, a hand-held device for screening high volumes of people and/or containers. In some cases, the device may be similar in appearance to devices disclosed in U.S. Pat. No. 6,558,626, incorporated herein by reference. In some cases, devices of the present invention provide a detector and sensor assembly suitable for the detection of a peroxide or peroxide precursor. In one embodiment, the device comprises an inlet for intake of a vapor sample (e.g., a vapor containing a peroxide), a sample cell comprising a peroxide-reactive material constructed and arranged to receive the vapor sample, and a detection mechanism in optical communication with the sample cell. In some cases, the device may not require an excitation source associated with the sample cell. In some cases, the detection mechanism may comprise a photodiode. In another embodiment, the device comprises an inlet for intake of a vapor sample, a sample cell comprising a material reactive with an explosive or a reactant or a decomposition product of the explosive, the sample cell constructed and arranged to receive the vapor sample, and a detection mechanism in optical communication with the sample cell, wherein the detection mechanism is free of an excitation source. In some cases, the device further comprises additional components, such as an apparatus for providing a continuous supply of the peroxide-reactive material to the sample cell or a component for reducing or otherwise controlling the amount of ambient light which enters the sample cell.

FIG. 3 illustrates, schematically, a system for determining an explosive according to one embodiment of the invention. A device 100 comprises an inlet 110 for intake of a vapor sample. Inlet 110 is connected to sample cell 120, which may comprise systems (e.g., solid-state or liquid-state peroxide-reactive, chemiluminescent systems) as described herein, such that a vapor sample entering sample cell 120 via inlet 110 may contact the system. Sample cell 120 may be constructed and arranged so that the vapor sample may pass across, over, or through the system, or in some way contact the system. A detector 130 is provided in optical communication with (e.g., connected to) sample cell 120 such that any light emitting from sample cell 120 may be collected, filtered, viewed, and/or stored/displayed by the detector. The detector may comprise a photomultiplier tube, a photodiode, or any apparatus for viewing the light emitted from sample cell 120. The detector may be configured to detect a particular range of emission, such as 400-700 nm (e.g., visible light), or 400-500 nm, or the like. The vapor sample may be removed from sample cell 120 via an outlet 140 connected to sample cell 120. Pump 150 may be connected to outlet 140 to remove the vapor sample from sample cell 120. Also, an out flow meter 160 may be used to regulate pump 150.

The inlet and outlet may be made of materials known in the art, such as polymer, metal, or other materials which may be inert to the vapor sample and/or otherwise suitable for constructing the device. Those of ordinary skill in the art, with the benefit of this disclosure, can readily select appropriate materials and construct a suitable system without undue experimentation.

Figure 4:
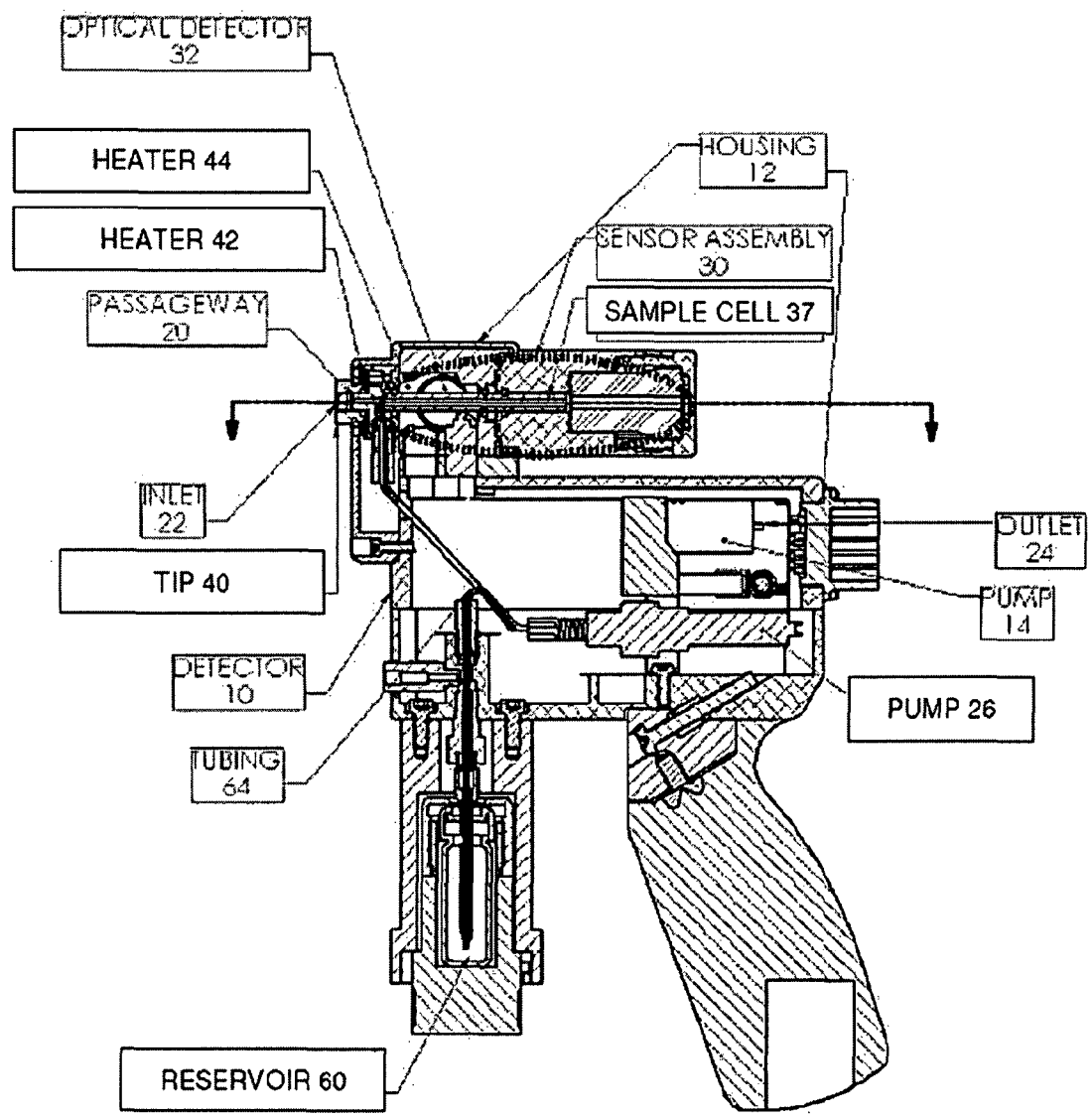
FIG. 4 illustrates, schematically, a sectional view of a detector, according to one embodiment of the invention.

In an illustrative embodiment, FIG. 4 shows a detector 10 for determination of a peroxide. Detector 10 may be a hand held device suitable for screening high volumes of people and containers. As shown in FIG. 4, apparatus 10 may comprise a sensor assembly 30 positioned within housing 12. Sensor assembly 30 may comprise a sample cell 37, which may contain a peroxide-reactive, chemiluminescent system as described herein. Passageway 20 may fluidly connect inlet 22, which is associated with tip 40, with outlet 24. Pump 14 may be associated with passageway 20 and may enable movement of a gases from inlet 22, through passageway 20, to outlet 24. Pump 14 may be an inline pump positioned within passageway 20, or may be otherwise positioned to be in fluid communication with passageway 20, to provide flow of a vapor sample suspected of containing vapor-phase hydrogen peroxide through detector 10. In some cases, an in-line flow meter may be employed to monitor gas flow through apparatus 10. The in-line flow meter may also be used to communicate with a microprocessor or other suitable device to control operation of pump 14, establishing a consistent flow of gas through detector 10.

Figure 5:
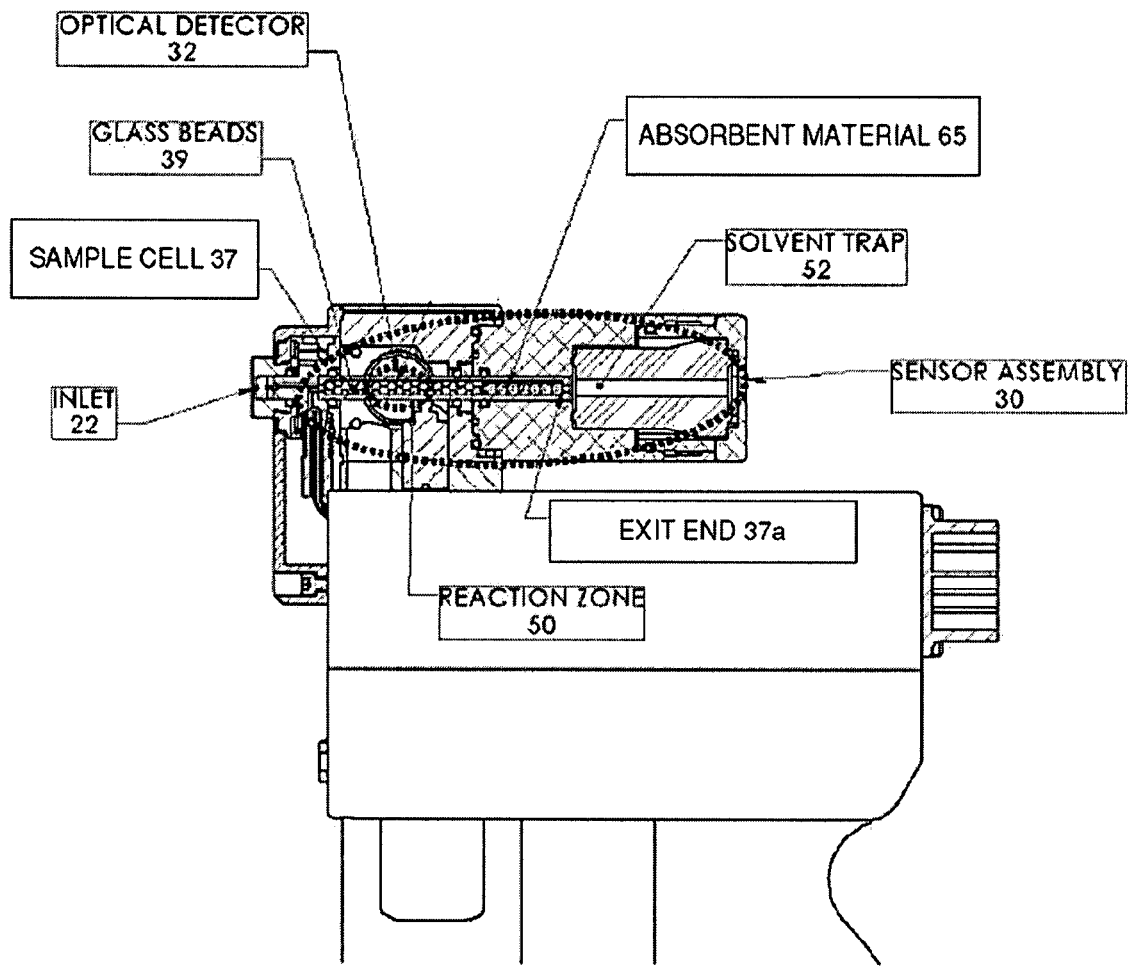
FIG. 5 illustrates, schematically, a sectional view of a sensor assembly housed within a detector, according to one embodiment of the invention.
Figure 6:
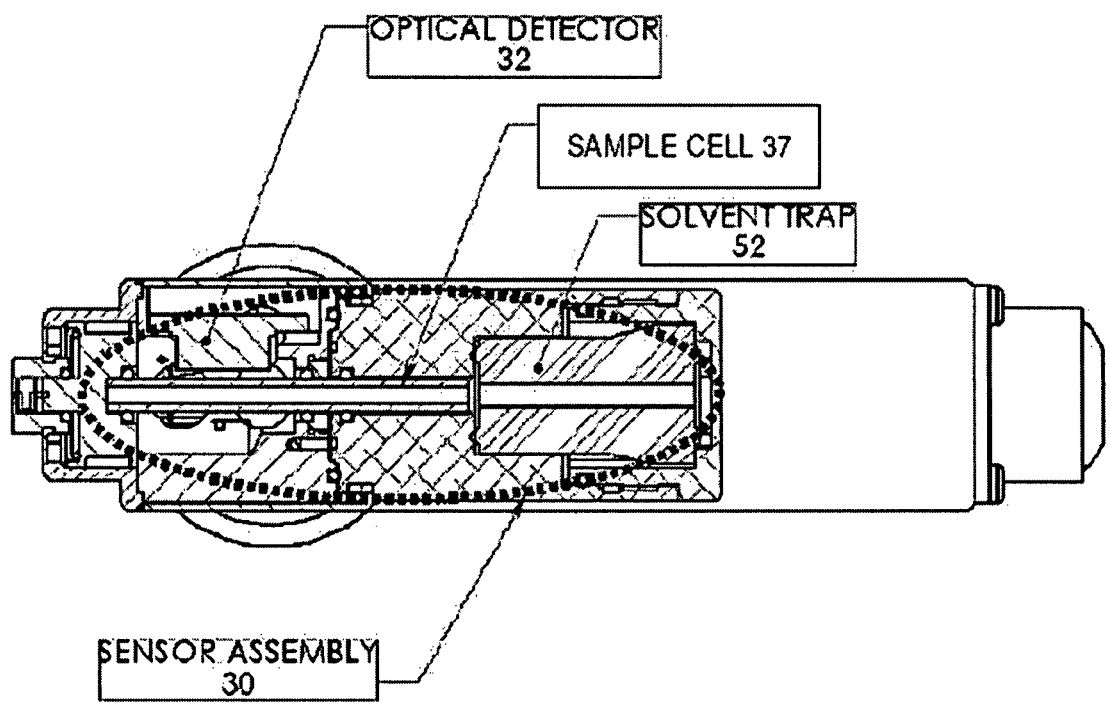
FIG. 6 shows, schematically, a sectional view of a sensor assembly, according to one embodiment of the invention.

Sensor assembly 30 may be positioned to be in fluid communication with passageway 20 such that vapors may contact the system. As shown in FIG. 5, sensor assembly 30 may include a sample cell 37 in fluid communication with inlet 22. The sample cell may also include a plurality of glass beads 39. A luminescent, peroxide-reactive system, as described herein, may be contained in sample cell 37, defining a reaction zone 50. Optical detector 32 may be positioned adjacent to sample cell 37 to allow for detection of emission generated as a result of the reaction between hydrogen peroxide and the luminescent, peroxide-reactive material. In some cases, optical detector 32 is a photodiode. Optical detector 32 may be advantageously positioned such that it does not contact vapors passing through sensor assembly 30. In one embodiment, optical detector 32 is located at the exit end 37a of sample cell 37 and is protected from the flow of gases by a transparent material, such as glass. In another embodiment, optical detector 32 may be positioned to the side of reaction zone 50, such that the optical detector is positioned in close proximity to reaction zone 50 thereby increasing the percentage of generated light reaching optical detector 32, i.e. this position improves the collection efficiency of optical detector 32. Additionally, sensor assembly 30 may comprise an adsorbent material 65 and/or solvent trap 52 (e.g., a carbon trap) positioned downstream from reaction zone 50. Solvent trap 52 may reduce the loss of, for example, solvent from the sample cell. Similarly, adsorbent material 65 can serve to capture excess system from the sample cell. Suitable electronics, software, and displays for measuring and communicating an emission detected by optical detector 32 are known to those of ordinary skill the art.

Detector 10 may also comprise reservoir 60, which may be arranged to contain the system, as described herein. (FIG. 4) Reservoir 60 may be fluidly connected to the sensor assembly via tubing 64. Fluid pump 62 can provide for movement of sensor material (e.g., the system) from reservoir 60 to sample cell 37. In some cases, reservoir 60 may be a glass vial, such as a silanized glass vial. In some cases, the use of reservoir 60 may remove the need to pre-coat sample cell 37 and/or beads 39 with the system prior to insertion into detector 10. Rather, reaction zone 50 may be coated or "primed" with the system prior to the first use of detector 10 by initially pumping an amount (e.g., about 2 μL to about 30 μL) of the system from reservoir 60 into sample cell 37. In some embodiments, 20 μL may be initially introduced into sample cell 37. Reservoir 60 may be arranged to contain sufficient volume of the system to permit operation of detector 10 for at least an eight hour period when about 1 μL to about 4 μL of system is provided to sample cell 37 about every fifteen minutes.

Figure 7A:
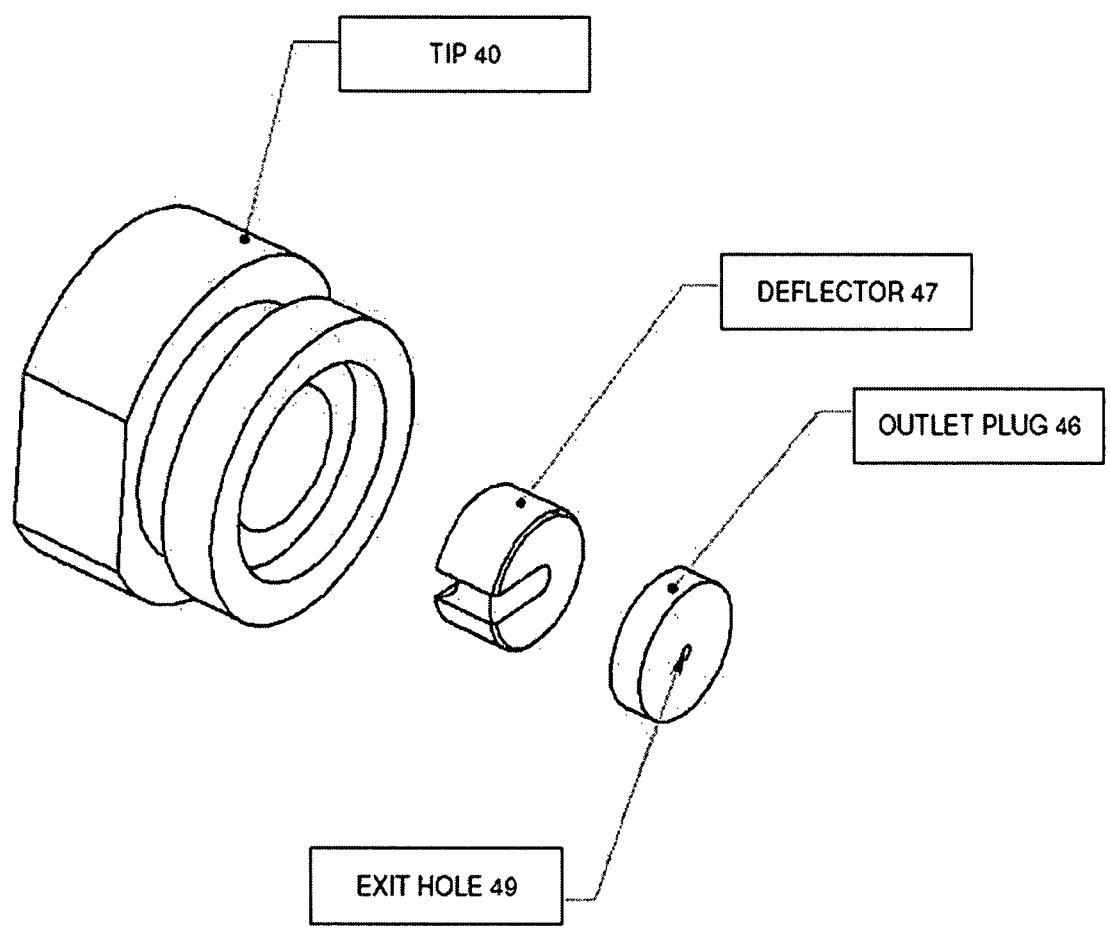
FIG. 7A show various components of a tip component of a detector, according to one embodiment of the invention.
Figure 7B:
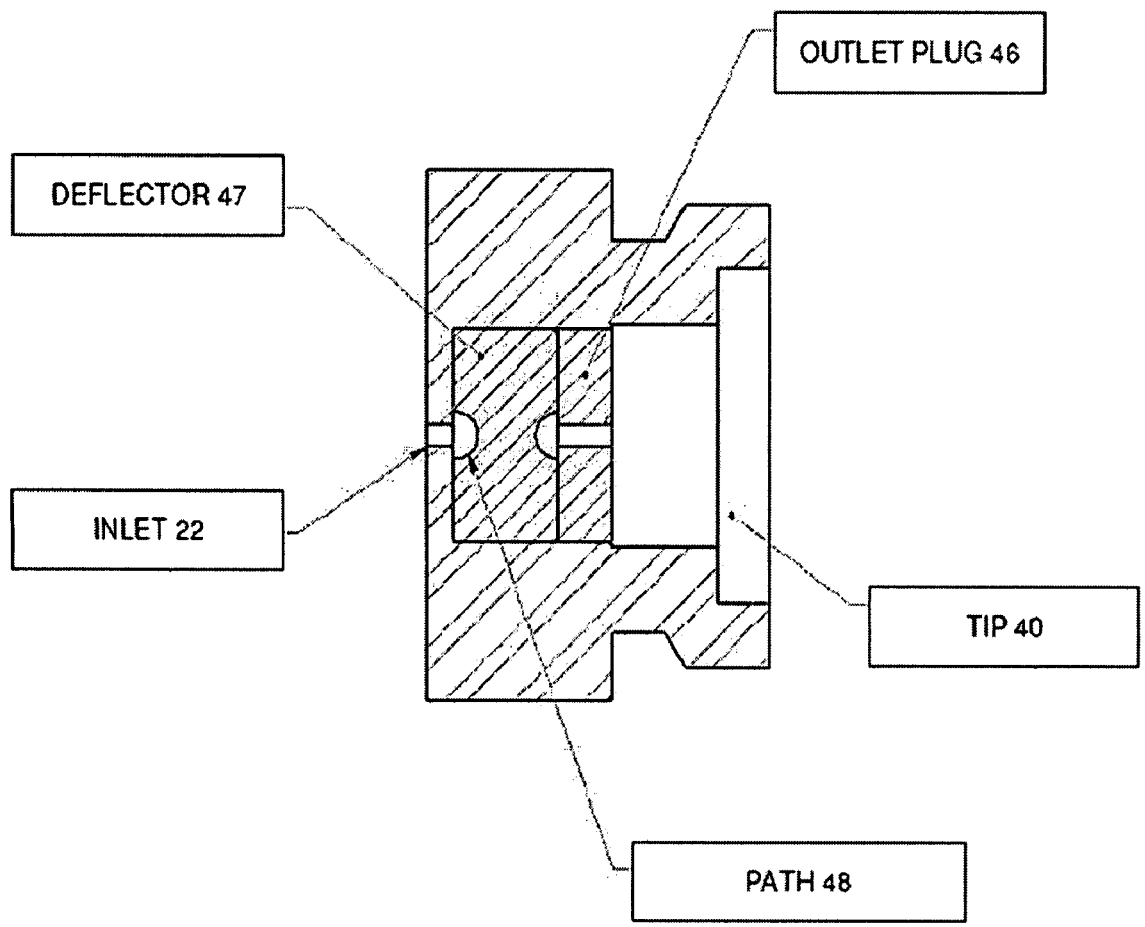
FIG. 7B shows a side view of a tip component of a detector, according to one embodiment of the invention.

To preclude or at least reduce the likelihood of a false positive by optical detector 32, inlet 22 may comprise a light-blocking tip 40 which, as a primary function, may substantially reduce and, in some cases, preclude, entry of ambient light into the area of detector 10 occupied by sensor assembly 30. (FIG. 4) For example, tip 40 may prevent ambient light from entering reaction zone 50. Additionally, tip 40 may enhance the collection of a vapor sample for determination. Inlet 22, sample cell 37, and outlet 24 may be fluidly connected such that a vapor may pass from inlet 22, through capillary 37, to outlet 24. Tip 40 may comprise inlet 22, which, as noted above, may be in fluid communication with passageway 20. FIG. 7 shows various components of tip 40 and FIG. 8 shows a side view illustration of tip 40 and its components, assembled. As shown in FIG. 7, tip 40 may include deflector 47 and outlet plug 46 which may be arranged to direct vapor entering inlet 22 through four 90° turns. This may allow tip 40 to substantially preclude penetration of ambient light to sensor assembly 30 without inhibiting gas sample flow. For example, as shown in FIG. 8, a vapor sample may pass through inlet 22 and encounter deflector 47 which includes a machined path 48 defining a path through tip 40. The vapor may then pass from path 48 through exit hole 49 of outlet plug 46, and may enter sample cell 37. In some cases, tip 40, deflector 47 and exit plug 46 may be prepared from stainless steel treated to substantially render the components inert to peroxide. For example, the components may be treated utilizing Restek's Sulfinert® or Siltek® coatings.

The rate of the reaction between hydrogen peroxide and the peroxide-reactive material can be improved by heating the vapor samples prior to entering sensor assembly 30 and contacting the peroxide-reactive material. Additionally, heating of tip 40 may reduce or preclude binding of peroxide molecules to tip 40, thereby further enhancing the sensitivity of detector 10. Tip 40 may be heated either directly or indirectly. Typically, a resistive type heater 42 can be positioned adjacent to tip 40 such that the temperature of tip 40 is between about 25° C. and about 100° C. In some cases, tip 40 may be maintained at a temperature of about 65° C. In general, the selection of temperature at tip 40 may be determined by the composition of the selected system.

Further, as shown in FIG. 4, detector 10 may include a heater 44 suitable for maintaining the temperature of the reaction zone 50 in the range of about 25° C. to about 150° C. In some embodiments, the temperature of reaction zone 50 may be about 55° C. However, the temperature of reaction zone 50 may be varied with the selection of the system. In general, the temperature for reaction zone 50 may be that temperature which provides the fastest reaction rate between hydrogen peroxide and the peroxide-reactive material. In one embodiment, a single heater 42 may be used to maintain the temperature of tip 40 and reaction zone 50.

Optionally, detector 10 can include a fan or other suitable cooling device. The fan may provide the ability to maintain reaction zone 50 in a desired temperature range when detector 10 is used in high temperature environments.

As described herein, devices of the invention may comprise a sample cell (e.g., capillary) in which systems of the invention may be contained. The sample cell may be constructed to provide sufficient surface area within the sample cell to promote reaction of the system (e.g., systems comprising a peroxide-reactive material) with hydrogen peroxide. The sample cell may also contain the system as a homogeneous and stable solution, dispersion, film, etc. In some cases, the sample cell may be selected to comprise a material that is substantially non-reactive with and non-degraded by one or more components of the system. In some cases, the sample cell may be treated (e.g., with silane and/or acid) to improve the shelf operational life of the system, i.e., may improve the chemiluminescent properties of the system. Some examples of such treatments are described in U.S. Pat. No. 3,974,368, incorporated herein by reference.

In some embodiments, the sample cell may be a transparent glass tube or capillary, which may be chemically etched to improve adhesion of the system. The capillary may optionally include irregular surfaces, including a serrated or fluted surface, for example. In some cases, the capillary may be positioned within an aluminum tube within sensor assembly 30. The aluminum tube may have a slot running along at least a portion of its length to permit transmission of light from the capillary to the optical detector. The aluminum tube may be attached to a heater by a thermocouple. A controller may supply power to the heater and may maintain the thermocouple at the desired setting. Optionally, a separate thermocouple or thermistor associated with the sensor assembly may monitor its temperature and may compensate for thermal drift.

In some cases, when the sample cell is a glass capillary, the system may be spin-coated on the interior of the capillary in liquid form. In some cases, capillary may have a length of about 4.5 cm to about 7.5 cm and an internal diameter of 3 mm. However, it should be understood that the size of the capillary is not considered to be limiting, with sizes ranging from small capillary sizes to larger diameters suitable for use in stationary devices. Suitable glass capillaries may be prepared from quartz, borosilicate, soda lime glass, flint glass and other similar naturally occurring and synthetic materials. Optionally, a portion of the capillary beyond the optical detector may contain or be coated with an absorbent material which can serve to capture excess system.

In the handheld device depicted in FIG. 4, sample cell 37 is a capillary carrying a sufficient layer of the system to react with vapor phase hydrogen peroxide and to generate detectable light. The layer comprising the system may have any thickness suitable for a particular application. In some cases, the layer of the system may be between about 2 μm and about 10 µm thick, or greater. Generally, the capillary may contain about 2 µL of spin-coated system such that the interior of the capillary defines the reaction zone 50.

In some cases, the sample cell may include additional components in order to increase the surface area of the reaction zone. For example, the sample cell may include beads (e.g., polymeric beads, glass beads, etc.) or other materials, optionally having irregular surfaces (e.g., serrated or fluted surfaces) placed within the sample cell. In some embodiments, the sample cell may include glass beads coated with the system and positioned within glass capillary 37, which can also be coated with the system. (FIG. 5) The coated beads may be retained within capillary 37 in a manner which readily permits passage of gases. For example, a short piece of plastic tubing sized to fit within capillary 37 but having an inner diameter smaller than beads 39 may retain the beads within the capillary. In general, any material which permits passage of gas without reacting therewith may be suitable for use in sample cells in the present invention. In one embodiment, the glass capillary may be transparent to the emission produced by the system, thereby permitting detection by optical detector 32. As described herein, the interior of the capillary may define the reaction zone 50. In some cases, the capillary may have a length of about 4.5 cm to about 7.5 cm and an internal diameter of 3 mm. Suitable glass capillaries may be prepared from quartz, borosilicate, soda lime glass, flint glass and other similar naturally occurring and synthetic materials.

The addition of glass beads, or other suitable materials, to the sample cell may increase the effective surface area of the sample cell, thereby allowing an increased volume of the system within the reaction zone. The volume of the system carried by beads may be sufficient to generate a detectible signal when exposed to vapor phase hydrogen peroxide. Typically, the amount of the system may be from about 40 µL to about 60 µL. In some cases, the sample cell is a glass capillary comprising glass beads contained within the glass capillary, such that the interior of the capillary and the surface of the glass beads define the area of the reaction zone. In some cases, the sample cell may contain about 50 µL of the system.

Additionally, the capillary and beads may be heat treated, i.e. sintered, to mechanically fuse the beads to the capillary. The capillary, beads, or fused bead/capillary configuration may be optionally treated to improve surface adhesion to prolong the luminescence lifetime of the system. For example, silane treatments and/or acid etching of the glass walls may enhance the adhesion of polymers to the walls of glass beads and capillaries, or may otherwise improve capillary performance.

The sample cell may have any shape, size, or other characteristic suitable for use in a particular application, such that the sample cell provides sufficient surface area for reaction between hydrogen peroxide and the system. In some cases, the sample cell may be easily replaceable. For example, a removable capillary having interior either coated with the system or comprising beads coated with the system may be useful in embodiments of the invention.

Devices as described herein may be useful in methods for the determination of peroxide-containing materials and other explosives. In some cases, the devices may be hand-held and/or portable, and may be used in a field environment such as airport security, sporting events, and field checkpoints.

In operation, detector 10 may be assembled and prepared for use in the determination of an analyte (e.g., a peroxide). For the purposes of this description, assembly may primarily concerned with installation of the sample cell 37 containing the system into sensor assembly 30, as shown in FIG. 4. Following assembly, tip 40 and reaction zone 50 may be heated to a desired operating temperature for the selected system. The operating temperature may vary depending on the components of the system. In some cases, the heating of tip 40 and reaction zone 50 may improve the reaction rate of reaction between the peroxide and the system. Prior to operation of detector 10, pump 14 may be turned on and tested to ensure operation within desired parameters. (FIG. 4) In general, pump 14 can provide a gas flow rate of about 20 $cm^3$/min to about 200 $cm^3$/min. However, it should be understood that any gas flow rate may be used to suit a particular application. In some embodiments, pump 14 permits adjustment of the flow rate to accommodate operational conditions. In some embodiments, an in-line flow meter may be used to monitor gas flow and/or to control operation of pump 14 in order to maintain a consistent flow of gas through detector 10.

Next, the sample cell may be placed within detector 10. In some cases, the sample cell may be a capillary or capillary containing beads, as described herein. In some cases, the system may be introduced into a sample cell positioned within the detector (e.g., "in situ"). For example, as shown in FIG. 4 pump 62 may be activated to supply an initial quantity of the system to reaction zone 50 from reservoir 60. Subsequently, during operation pump 62 may be activated from time to time to maintain a sufficient quantity of the system in reaction zone 50 to react with hydrogen peroxide. As discussed above, the initial quantity of the system may be typically about 20 µL and subsequent dosing can occur about every 15 minutes. Subsequent dosing of the system may involve introducing between about 1 µL to about 4 µL of the system to sample cell 37. In some cases, the operator of the device may have the option of adjusting this amount based on operating conditions.

Following set up of detector 10, initial testing of a known sample may be performed to allow the operator to test the operation of the sensor assembly to ensure sufficient dosing and functionality of the system. In particular, the testing may ensure that optical detector 32 is properly aligned with reaction zone 50 to produce a sufficient and positive response when the test sample reacts with the system. When used in the field, detector 10 may be operated by placing tip 40 in the vicinity of an object of interest. For example, for trace detection of analytes, tip 40 may be positioned less than 75 mm from the source. With pump 14 operating, a flowing gas stream can enter passageway 20 at a rate between about 30 $cm^3$/min and 200 $cm^3$/min. In some cases, the flow rate is about 120 $cm^3$/min. The flow rate through detector 10 may be affected by the size of reaction zone 50. For example, a higher flow rate may be used for larger reaction zones.

The gas or vapor sample may be heated as it is passed through tip 40. As described herein, tip 40 may be heated to a temperature between the range of about 25° C. and about 100° C. In some cases, tip 40 may be maintained at a temperature of about 65° C., heating the vapor sample to about 60° C. as it flows through tip 40. The vapor sample may be subsequently passed through passageway 20 into sensor assembly 30 where it may enter reaction zone 50 at a flow rate of between about 20 $cm^3$/min. to about 200 $cm^3$/min. for a capillary having an inner diameter of about 0.5 mm to about 10 mm. Reaction zone 50 may be generally heated to a temperature between about 25° C. to about 150° C. In some embodiments, the temperature of reaction zone 50 may be about 55° C. As described herein, the operating temperatures for tip 40 and reaction zone 50 may vary with the composition of the system.

Within reaction zone 50, vapor-phase peroxide present in the gas can react with the peroxide-reactive material of the system to produce energy in the form of the emission of a photon. In some cases, the resulting energy can stimulate luminescence of the light-emitting material such that light energy is emitted. In some cases, an emission may be produced in the visible range. In some cases, an emission may be produced outside the visible range. The resulting emission may be detected by optical detector 32 which can transmit a signal to a display device associated with or incorporated into detector 10.

Typical reaction times for producing a light response may range between about 1 second to about 20 seconds. In some embodiments, the reaction time is less than five seconds. Additionally, the system may be selected to provide a fast recovery time following a positive test result. In general, the system can return to its original state, i.e., can recover, from a positive test result in about 60 seconds or less, or, in some cases, about ten seconds or less, after the exposure to the hydrogen peroxide vapor has ceased. In some cases, the system can recover and can be ready for exposure to another vapor sample within five seconds or less. Finally, detector 10 may be operated under conditions of temperature, flow rate and the selected system which provide a sensitivity such that vapor-phase peroxide as low as 10 parts per billion (ppb) may be detected by this method.

Thus, the method of the current invention does not require prior processing of a vapor-phase hydrogen peroxide. Rather, the current invention permits immediate processing of gases suspected of containing vapor-phase hydrogen peroxide. Accordingly, the methods and apparatus of the current invention are well suited to the field environment where rapid testing of suspected materials for trace amounts of hydrogen peroxide is critical.

Device of the invention may be useful in various applications. As described herein, the devices may be useful as hand-held and/or portable devices. In some cases, larger units suitable for stationary monitoring may also be utilized.

Devices, systems and methods of the present invention may be advantageous in that they allow for the determination (e.g., detection) of peroxides, peroxide precursors, explosives, and/or other species using a liquid-state or solid-state system. Other detection methods may require delicate optics configurations, high power lasers, complex sampling apparatuses, external means for photodetection and signal amplification (e.g., a photomultiplier tube), and the like. Such equipment can prove costly to fabricate and operate, and can add bulk to the device. Devices of the present invention may eliminate the need for complex sampling and detection equipment, providing simplified, devices amenable to in-field use. In some cases, the devices may be disposable. In some cases, the device may have a strong signal response against a near-zero background (e.g., a high signal-to-noise ratio). Such devices may be easy to fabricate and operate.

The peroxide-reactive material may be any material which can interact (e.g, undergo a chemical reaction) with a peroxide molecule, resulting in the generation an observable signal (e.g., light emission). The interaction may directly generate the signal or may initiate a series of chemical reactions which leads to the generation of the signal. For example, the peroxide-reactive material may react with a peroxide to produce a photon of light in the visible spectrum. In some embodiments, the peroxide-reactive material is a compound having the formula,

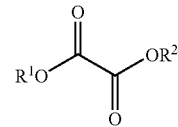

wherein $R^1$ and $R^2$ are independently aryl, substituted aryl, heteroaryl, or substituted aryl. In some embodiments, the aryl or heteroaryl group may be substituted with hydrogen, hydroxy, halide, a carbonyl group, an optionally substituted amine, optionally substituted alkyl, optionally substituted alkoxy, cyano, and/or nitro group. Specific examples include bis(2-carbopentyloxy-3,5,6-trichlorophenyl oxalate, bis(2-nitrophenyl) oxalate, bis(2,4-dinitrophenyl) oxalate, bis(2,6-dichloro-4-nitrophenyl) oxalate, bis(2,4,6-trichlorophenyl) oxalate, bis(3-trifluoromethyl-4-nitrophenyl) oxalate, bis(2-methyl-4,6-dinitrophenyl) oxalate, bis(1,2-dimethyl-4,6-dinitrophenyl) oxalate, bis(2,4-dichlorophenyl) oxalate, bis (2,5-dinitrophenyl) oxalate, bis(2-formyl-4-nitrophenyl) oxalate, bis(pentachlorophenyl) oxalate, bis(pentafluorophenyl) oxalate, bis(1,2-dihydro-2-oxo-1-pyridyl) glyoxal, bis-N-phthalmidyl oxalate, bis(2,4,5-trichloro-6-carbopentoxyphenyl) oxalate, bis(2,4,5-trichloro-6-carbobutoxyphenyl) oxalate, bis(2,4,6-trichlorophenyl) oxalate, bis(2,4,5-trichloro-6-carbopentoxyphenyl) oxalate, bis(2,4,5-trichloro-6-carbobutoxyphenyl) oxalate, bis(2,4,6-trichlorophenyl) oxalate, and phthalimido 3,6,6-trisulfo-2-naphthyl oxalate. Other examples of peroxide-reactive materials include 5-amino-2,3-dihydrophthalazine-1,4-dione or 3-aminophthalhydrazide luminol), Cyalume® (containing diphenylethandioate, a dye, and other components) 2,4,5-triphenylimidazole (lophine), 10,10'-dialkyl-9,9'-biacridinium salts (lucigenin), and 9-chlorocarbonyl-10-methylacridinium chloride (rosigenin), and the like. In some embodiments, the peroxide-reactive material is bis(2,4,6-trichlorophenyl) oxalate, bis(2-carbopentyloxy-3,5,6-trichlorophenyl)oxalate, or oxalic acid bis[2,4,5-trichloro-6-(pentyloxycarbonyl)phenyl]ester. In a particular embodiment, bis(2,4,6-trichlorophenyl) oxalate is the peroxide-reactive material. In another embodiment, bis(2-carbopentyloxy-3,5,6-trichlorophenyl) oxalate is the peroxide-reactive material.

Other examples of suitable peroxide-reactive materials include oxamides, as represented by the structure,

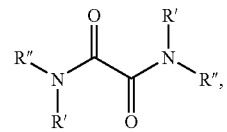

wherein R' and R" can be the same or different, and R' can be trifluoromethane sulfonyl, 2,4,5-trichlorophenyl, 2,3,4,5,6-pentafluorophenyl, 2,4-dinitrophenyl, phenyl, or other substituted derivatives thereof. In some cases, R' and/or R" may comprise an electron-withdrawing group, such as nitro, cyano, carbonyl groups (e.g., aldehydes, ketones, esters, etc.), sulfonyl, trifluoromethyl, and the like.

In some embodiments, the peroxide-reactive material may be present in an amount of about 25 weight % or greater, or, in some cases, 50 weight %, 75 weight %, or 95 weight % or greater. In some cases, the peroxide-reactive material may be present in an amount of about 50 weight %. In an illustrative embodiment, the system comprises 49.875 weight % of the peroxide-reactive material.

Light-emitting materials suitable for use in the present invention may be any luminescent material, including dyes, oligomers, polymers, combinations thereof, etc. The light-emitting material may be selected to exhibit certain properties, such as a particular emission wavelength, high quantum yield, high output light efficiency when formulated in a peroxide reactive system, and/or compatibility (e.g., solubility) with one or more components of the system. For example, the light-emitting material may be selected to be soluble with respect to a solvent or other carrier to form mixtures (e.g., solutions) having a high concentration of the light-emitting material, e.g., at least 0.15 weight %, at least 0.25 weight %, or greater. In some embodiments, the light-emitting material may be selected to exhibit a high quantum yield, for example, when present in a system having a high concentration of light-emitting material. As used herein, the "quantum yield" of a material refers to the total emission produced by the material, i.e., the number of photons emitted per absorbed photon. In some cases, the light-emitting material may have a quantum yield of at least 50%, at least 75%, at least 90%, at least 95%, or, in some cases, at least 99% or greater. In some embodiments, the light emitting material may be selected to exhibit a high output light efficiency when formulated in a peroxide reactive system. As used herein, "output light efficiency" of a material in the system refers to the yield of output light (e.g., observable light) produced by the system in the presence of a peroxide, i.e., the efficiency of the interaction between the peroxide and the system in generating light.

In some cases, light-emitting materials may be any compound which has a determinable emission of light (e.g., chemiluminescence, fluorescence, phosphorescence), typically with an emission spectrum between 330-1200 nm. In some embodiments, the emission spectrum is between 400-700 nm. In some embodiments, the presence of a peroxide or peroxide precursor does not affect the ability of the light-emitting material to generate a determinable signal. In some embodiments, the light-emitting material is a fluorescent dye. Light-emitting materials are known in the art and are described in "Fluorescence and Phosphorescence," by Peter Pringsheim, Interscience Publishers, Inc., New York, N.Y., 1949, and "The Color Index," Second Edition, Volume 2, The American Association of Textile Chemists and Colorists, 1956. Additional light emitting materials are disclosed by U.S. Pat. Nos. 3,749,679 and 6,126,871 incorporated herein by reference. Examples of suitable light-emitting materials include anthracene, benzanthracene, phenanthrene, naphthacene, pentacene, substituted derivatives thereof, and the like. Examples of substituents include phenyl, lower alkyl, halide, cyano, alkoxy, and other substituents which do not interfere with the light-emitting reaction described herein. Additionally, any combination of light-emitting materials may be used to, for example, advantageously alter the wavelength of emitted light, the intensity of emitted light, and the like.

In some embodiments, the light-emitting material may comprise a rigid, shape-persistent portion which may improve various properties of the materials including solubility and/or emissive properties of the materials. As used herein, a "shape-persistent portion" of a molecule is a portion having a molecular weight of at least 15 g/mol and having a significant amount of rigid structure, as understood by those of ordinary skill in the art. As used herein, a "rigid" structure means a structure, the ends of which are separated by a distance which cannot change (outside of normal molecule-scale changes in temperature, etc.) without breaking at least one bond, as understood by those of ordinary skill in the art. In some embodiments, the shape-persistent portion may have a molecular weight of at least 25, 50, or 100 g/mol. Generally, the shape-persistent portion may not move relative to other portions of the molecule via, for example, rotation about a single bond. For example, the shape-persistent portion may comprise an aromatic ring structure fused to a portion of the polymer via two adjacent atoms of the polymer, such that the shape-persistent portion may not rotate relative to the two adjacent atoms of the polymer.

Shape-persistent structures may be provided, for example, by aromatic groups, bridged, bicyclic and polycyclic structures, and the like. For example, an iptycene molecule is a shape-persistent portion. By contrast, a molecule including a cyclic structure such as a benzene ring connected to another portion of the molecule via only a single bond, such as in a biphenyl group, has at least a portion of the molecule that is not shape-persistent, since a benzene ring can rotate about a single bond.

Some examples of shape-persistent portions include planar structures, such as aromatic groups (e.g., benzenes, naphthalenes, pyrenes, etc.). The aromatic groups may be rigidly bonded to (e.g., fused to) the light-emitting material, i.e., the aromatic group is bonded to the light-emitting material via two covalent bonds at adjacent positions on the aromatic ring. In some cases, the shape-persistent portion includes a non-planar structure, such as a bicyclic or polycyclic structure wherein bridgehead atoms are not positioned adjacent to one another within the molecule. Examples include adamantanes, norbornenes, iptycenes, and the like. In one embodiment, the shape-persistent portion comprises a bicyclic ring system that is non-planar (e.g., an iptycene).

In some embodiments, the light-emitting material or may comprise an iptycene. An iptycene typically comprises arene planes fused together via at least one [2.2.2]bicyclooctane moiety. Examples of iptycenes include triptycenes (3 arene planes) and pentiptycenes (5 arene planes). For example, the light-emitting material may comprise anthracene covalently bonded to an iptycene. In one embodiment, the light-emitting material may have the following structure,

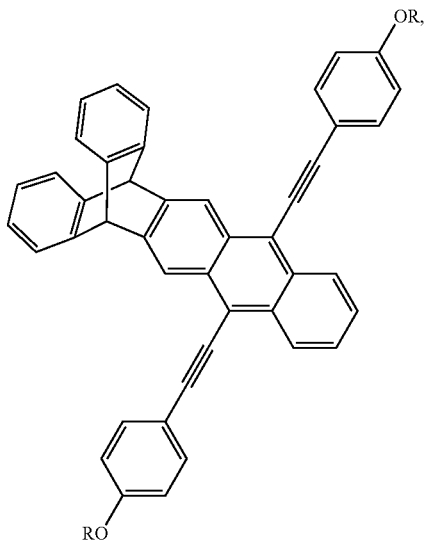

wherein R is alkyl, heteroalkyl, aryl, or heteroaryl. In one embodiment, R is alkyl, such as octyl.

In one embodiment, the light-emitting material is anthracene, diphenylanthracene, 9,10-bis(phenylethynyl)anthracene, or a material comprising anthracene covalently bonded to an iptycene. In one embodiment, the light-emitting material is 9,10-bis(phenylethynyl)-anthracene, or a substituted derivative thereof.

In some embodiments, the light-emitting material may be a conjugated polymer, such as poly(phenylene-ethynylene), poly(phenylene-vinylene), poly(p-phenylene), polythiophene, other poly(arylene)s, substitute derivatives thereof, and the like. The light-emitting capability of such polymers are known in the art, and can be selected to suit a particular application.

In some embodiments, the light-emitting material may be covalently bound to the peroxide-reactive material. In some embodiments, the light-emitting material may be covalently bound to the support material.

In certain embodiments, a peroxide-reactive material may be converted into a light-emitting material by interaction with a peroxide or peroxide precursor. For example, in the presence of a peroxide, peroxide-reactive 3-amino-phthalhydrazide ("luminol") forms an excited state aminophthalate ion and may be converted to a light-emitting material through the relaxation of the excited state to the ground state, emitting a chemiluminescent signal.

The support material may be any material (e.g., liquid, solid, etc.) capable of supporting (e.g., containing) the components (e.g., the peroxide-reactive material, the light-emitting material, etc.) of the systems described herein. For example, the support material may be selected to have a high boiling point, such as a boiling point of at least 300° C. or greater, or, in some cases, at least 400° C., 500° C., or greater. The support material may also be selected to have low vapor pressure. In some cases, the support material may be a material that may remain in the solid state at room temperature (e.g., 25° C.) but may undergo transition to a liquid state at temperatures lower than or at the operating temperature of the device.

In some cases, the support material may be selected to have a particular surface area wherein the support material may absorb or otherwise contact a sufficient amount of analyte (e.g., organic peroxide explosive) to allow interaction between the analyte and, for example, the peroxide-reactive material. In some embodiments, the support material has a high surface area. In some cases, the support material has a surface area of at least 50 $mm^2$, at least 100 $mm^2$, at least 200 $mm^2$, at least 300 $mm^2$, at least 400 $mm^2$, or, more preferably, at least 500 $mm^2$. In one embodiment, the support material may be filter paper having a surface area of at least 50 $mm^2$, or as otherwise described herein.

In some embodiments, the support material may preferably have a low background signal, substantially no background signal, or a background signal which does not substantially interfere with the signal generated by the system in the presence of a peroxide or peroxide precursor. In some cases, the support material may have a preferred pH to prevent undesirable reactions with, for example, an acid. The support material may be soluble, swellable, or otherwise have sufficient permeability in systems of the invention to permit, for example, intercalation of the peroxide-reactive material, the light-emitting material, the catalyst, and other components of the system within the support material. In one embodiment, the support material may be hydrophobic, such that a hydrophobic solution containing the peroxide-reactive material, the light-emitting material, and, optionally, catalyst, may diffuse or permeate the support material. Additionally, the support material may preferably permit efficient contact between the sample (e.g., peroxide or peroxide precursor) to be determined and the peroxide-reactive material. For example, in one embodiment, a vapor comprising a peroxide may permeate the support material to interact with the peroxide-reactive material. The permeability of certain support materials described herein are known in the art, allowing for the selection of a particular support material having a desired diffusion. The choice of support material may also affect the intensity and duration of light emission from the system.

In some cases, the support material may be a liquid, such as liquid having low volatility or a low or negligible vapor pressure. Use of a liquid support material may, in some cases, enhance the reaction (e.g., reaction rate) between peroxide vapor and the peroxide-reactive material by providing systems of the invention in a homogeneous solution. The liquid may have a boiling point of at least 300° C., at least 400° C., at least 500° C., or greater. As used herein, the "boiling point" refers to the boiling point of a material at atmospheric pressure (e.g., about 1 atm). Examples of liquid support materials (e.g., solvents) include, but are not limited to, dicyclohexyl phthalate or dioctyl terephthalate. In some cases, the solvent may be an ionic liquid. In some cases, the ionic liquid may be capable of functioning as a catalyst during the chemiluminescence reaction. As used herein, the term "ionic liquid" is given its ordinary meaning in the art and refers to a liquid comprising primarily ionic species. That is, at equilibrium, greater than 90% of species in an ionic liquid may be ionic. In some embodiments, greater than 99%, or, greater than 99.9%, of species in an ionic liquid may be ionic. In some cases, the ionic liquid is a salt. Examples of ionic liquids include ethylammonium nitrate and imidazolium salts.

In some cases, the support material may be a solid. Examples of solid support materials include glass supports, polymers, copolymers, gels, solid adsorbent materials such as Kim Wipes® and filters. In some embodiments, the support material may be a finely divided powder, particles, molded shapes such as beads, films, bottles, spheres, tubes, strips, tapes, and the like. The support material may be glass wool, glass filter paper, filter paper, nylon filters, and the like. In one embodiment, the support material is a powder. In one embodiment, the support material is a silica. In some embodiments, the system may have a shape or be formed into a shape (for example, by casting, molding, extruding, and the like). In some embodiments, the support material may be a film, a bottle, a sphere, a tube, a strip such as an elongated strip or tape, or the like.

In some embodiments, the support material may be a polymer. Examples include polyethylene, polypropylene, poly(vinyl chloride), poly(methyl methacrylate), poly(vinyl benzoate), poly(vinyl acetate), cellulose, corn starch, poly(vinyl pyrrolidinone), polyacrylamide, epoxys, silicones, poly(vinyl butyral), polyurethane, nylons, polacetal, polycarbonate, polyesters and polyethers, crosslinked polymers such as polystyrene-poly(divinyl benzene), polyacrylamide-poly(methylenebisacrylamide), polybutadiene copolymers, combinations thereof, and the like. In a particular embodiment, the polymer is corn starch.

The combination of support material and solvent may have a desired diffusion rate, controlling the intensity and duration of light emission. The permeability of a particular polymer is known in the art. Examples include polystyrene-poly(divinyl benzene) copolymer and ethylbenzene, poly(vinyl chloride) and ethyl benzoate, and poly(methyl methacrylate) and dimethylphthalate.

The support material may be formed in a variety of ways. The flexibility of the materials may be tuned to fit a desired application by methods known in the art. For example, the addition of plasticisizers, or use of a rubber base, such as silicone. The usual monomeric and preferably oligomeric plasticizers known in the state of the technology can be used within the meaning of the invention, alone or mixed with the polymeric plasticizers. These are, for example, phthalates (phthalic acid esters) such as dioctyl phthalate (DOP), diisononyl phthalate (DINP), diisodecyl phthalate (DIDP), dibutyl phthalate (DBP), diisobutyl phthalate (DIBP), dicyclohexyl phthalate (DCHP), dimethyl phthalate (DMP), diethyl phthalate (DEP), benzyl-butyl phthalate (BBP), butyl-octyl phthalate, butyl-decyl phthalate, dipentyl phthalate, dimethylglycol phthalate, dicapryl phthalate (DCP) and the like; trimellitates, such as, in particular, trimellitic acid esters with (predominantly) linear C6 to C11 alcohols with low volatility and good cold elasticity, acyclic (aliphatic) dicarboxylic acid esters, such as, in particular, esters of adipic acid, such as dioctyl adipate (DOA), diisodecyl adipate (DIDA), especially mixed with phthalates; dibutylsebacate (DBS), dioctyl sebacate (DOS) and esters of azelaic acid, especially mixed with phthalates, dibutyl sebacate; oligomeric plasticizers such as polyesters of adipic, sebacic, azelaic and phthalic acid with diols such as 1,3-butanediol, 1,2-propanediol, 1,4-butanediol, and 1,6-hexanediol, and with triols such as, especially, glycerin and more highly functional alcohols, phosphates (phosphoric acid esters), especially tricresyl phosphate (TCP), triphenyl phosphate (TPP), diphenyl cresyl phosphate (DPCP), diphenyloctyl phosphate (DPOP), tris-(2-ethylhexyl) phosphate (TOP), tris-2-butoxyethyl) phosphate, fatty acid esters, such as, in particular, butyl stearate, methyl and butyl esters of acetylated ricinol fatty acid, triethylene glycol-bis-(2-ethylbutyrate), hydroxycarboxylic acid esters such as, in particular, citric acid esters, tartaric acid esters, lactic acid esters, epoxide plasticizers, such as, in particular, epoxidized fatty acid derivatives, especially triglycerides and monoesters, and the like, such as are known particularly as PVC plasticizers. In this connection, see Rompp Chemie Lexikon, 9th Ed., Vol. 6, 1992, pp. 5017-5020.

The catalyst may be any material which enhances the ability of the system to emit light. In some cases, the catalyst may accelerate the rate of response of the system to a peroxide. For example, in the illustrative embodiment shown in FIG. 2, the addition of sodium salicylate may facilitate the reaction between the oxalic ester and peroxide to form the strained cyclic intermediate, resulting in accelerated signal generation (e.g., light emission). Examples of suitable catalyst may include basic catalysts including amines, hydroxides, alkoxides, carboxylic acid salts and phenolic salts. In some cases, the catalyst may be a carboxylic acid and phenol whose conjugate acid has pKa values between 1-6 in neat water. Some examples include sodium salicylate, tetrabutylammonium salicylate, potassium salicylate, tetrahexylammonium benzoate, benzyltrimethylammonium m-chlorobenzoate, dimagnesium ethylenediamine tetraacetate, tetraethyl ammonium stearate, calcium stearate, magnesium stearate, calcium hydroxide, magnesium hydroxide, lithium stearate, triethylamine, pyridine, piperidine, imidazole, triethylene diamine, potassium trichlorophenoxide. In a particular embodiment, the catalyst is sodium salicylate.

Solvents which may be used in methods of the invention may include any solvent capable of forming fluid mixture, a suspension, or a homogeneous solution with the components of the system In some cases, the solvent is hydrophobic. Examples may include acyclic or cyclic ethers, such as ethylene glycol ethers, diethyl ether, diamyl ether, diphenyl ether, anisole, tetrahydrofuran, and dioxane, esters such as ethyl acetate, propyl formate, amyl acetate, dialkyl esters of phthalic acid (e.g., dimethyl phthalate, diethyl phthalate, dibutyl phthalate, dioctyl phthalate), methyl formate, triacetin, diethyl oxalate, dioctyl terphthalate, citric acid esters, methyl benzoate, ethyl benzoate, and butyl benzoate, aromatic hydrocarbons, such as benzene, ethyl benzene, butyl benzene, toluene, and xylene, chlorinated hydrocarbons, such as chlorobenzene, o-dichlorobenzene, m-dichlorobenzene, chloroform, carbon tetrachloride, hexachloroethylene, tetrachlorotetrafluoropropane, and the like. In one embodiment, dibutyl phthalate is preferred. In one embodiment, toluene is preferred.

Additionally, other components may be added to systems of the invention. For example, a buffer may added to produce a desired pH of the system. In some embodiments, an acid may be added. In some embodiments, a base may be added. In some cases, the acid and/or base may preferably be inert to the components of the system (e.g., peroxide-reactive material, light-emitting material, catalyst, support material, etc.) Examples of bases which may be used in the invention include inorganic and organic bases, such as sodium hydroxide, potassium hydroxdie, potassium t-butoxide, sodium ethoxide, sodium methoxide, ammonium hydroxide, t-butylammoniuim hydroixde, tripheynl methide, Lewis bases, including pyridine, triethylamine, quinoline, combinations thereof, and the like. Examples of suitable acids include hydrochloric, hydrobromic, sulphuric, nitric, perchloric, fumaric, maleic, phosphoric, glycollic, lactic, salicyclic, succinic, toluene-p-sulphonic, tartaric, acetic, citric, methanesulphonic, formic, benzoic, malonic, naphthalene-2-sulphonic, trifluoroacetic and benzenesulphonic acids, combinations thereof, and the like.

Also, a material capable of decreasing the amount of background peroxide may be optionally included in systems and devices of the invention. For example, enzymes, such as horseradish peroxidase or other catalases, may breakdown background hydrogen peroxide.

EXAMPLES

Example 1

Sample cells comprising systems as described herein were prepared using frosted glass capillaries with frosted glass beads (2 mm in diameter) contained within the capillaries. A capillary was filled with 25 frosted glass beads, and the ends of the capillary were fitted with tubing and capped. The capillary was then filled with about 225-250 microliters of chemiluminescent solution extracted from a Cyalume® lightstick, and the sample cell was sealed. The sample cells were then stored in a Mylar® bag at room temperature until needed, upon which the cap was removed and excess solution was manually blotted. Alternatively, the excess solution may be removed by vapor or vacuum introduction.

Figure 8D:
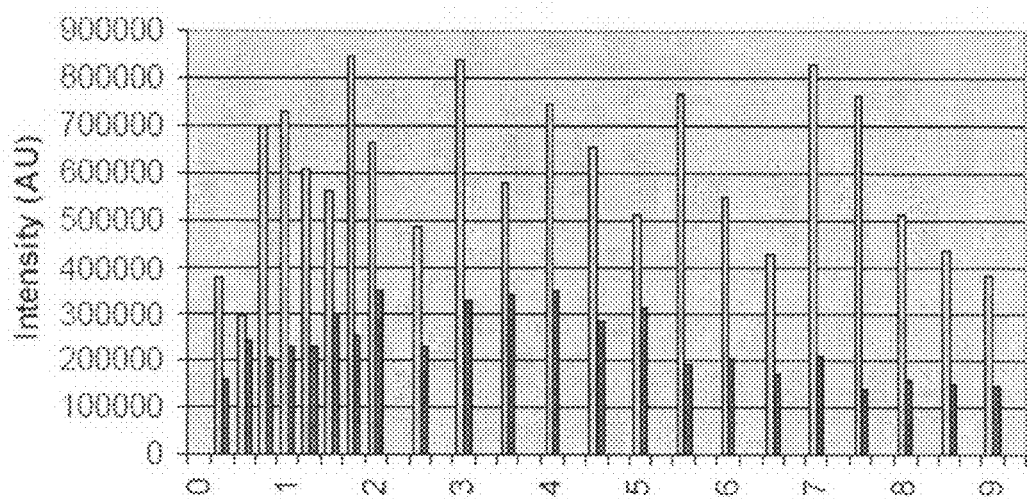
FIG. 8 shows the luminescence intensity response of a system of the invention as a function of time, upon exposure to a head-space peroxide vapor (left columns) and from exposure to the inside surface of a vial containing a peroxide (right columns) after (a) 1 day, (b) 2 days, (c) 8 days, (d) 23 days, and (e) upon exposure to the inside surface of a vial containing a peroxide after 39 days.
Figure 8E:
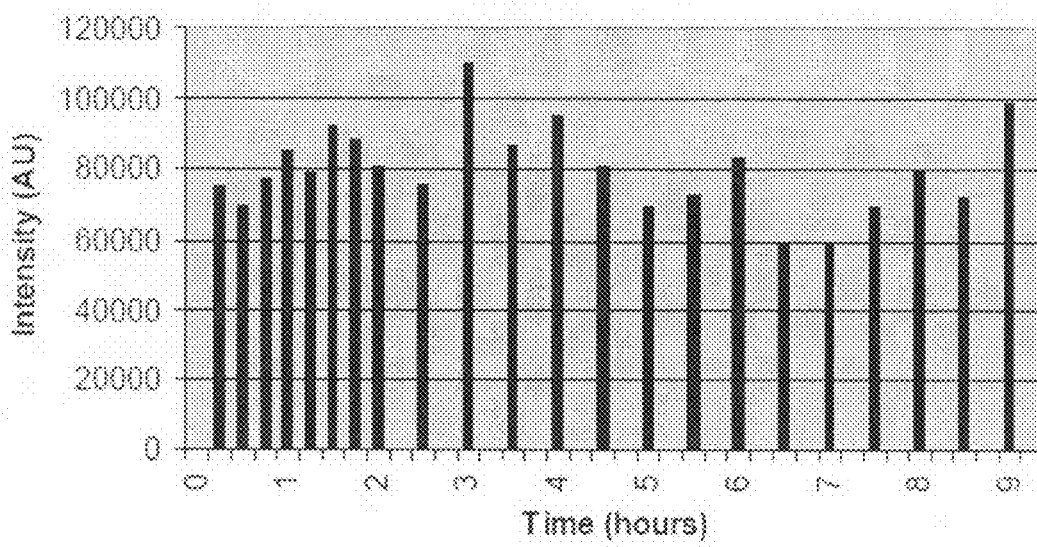

The peroxide sensing experiments were carried out on a commercial Fido™ instrument manufactured by Nomadics Inc., which continuously monitors the total luminescence during vapor sampling. The frosted beads served to increase the overall surface area, trapping more chemiluminescent solution, but did not impede vapor flow within the capillary. Data was obtained from a freshly prepared capillary, challenged with 1 cc of head-space vapor of urea-peroxide crystals delivered via syringe. Alternatively, the capillary may be exposed for one-second to the lid (inside surface) of a sample vial containing urea-peroxide crystals. FIG. 8 shows the luminescence intensity of the material as a function of time, with results from exposure to a head-space vapor (left columns) and from exposure to a vial lid (inside surface) (right columns) after (a) 1 day, (b) 2 days, (c) 8 days, (d) 23 days, and (e) the results from exposure to a vial lid (inside surface) after 39 days. As shown in FIGS. 8A-E, the capillary remained active towards peroxide vapor for a considerable length of time.

Example 2

In devices and methods of the invention, solvent evaporation may present a challenges for embodiments using a liquid chemiluminescent system (e.g., a "wet capillary" system). For example, periodic cleaning of the Fido™ optics was required, and pump damages was observed. To address this issue, chemiluminescent solution was extracted from three Cyalume® lightsticks (about 8 mL) and was combined with dioctyl terephthalate (DOTP) (8 mL). DOTP was selected for its high boiling point of 400° C. and its low toxicity, relative to other plasticizers. The resulting solution was vacuum distilled to removed the problematic volatile solvent, butyl benzoate, which has a boiling point of 249° C. The capillaries were prepared using 50 microliters of the DOTP-modified chemiluminescent solution under anhydrous/anaerobic conditions to preserve activity. Peroxide sensing tests as described in Example 1 yielded comparable results to the "parent" butyl benzoate system, with the exception that solvent condensation on the optics of the detectors was not observed, even after ~24 hours of continuous testing (65/55° C., 120 ccm). The replacement of butyl benzoate with DOTP eliminates the need to periodically clean the Fido optics and prevents deterioration of the pump. The shelf-life of the DOTP-modified chemiluminescent solution was also monitored.

Figure 10A:
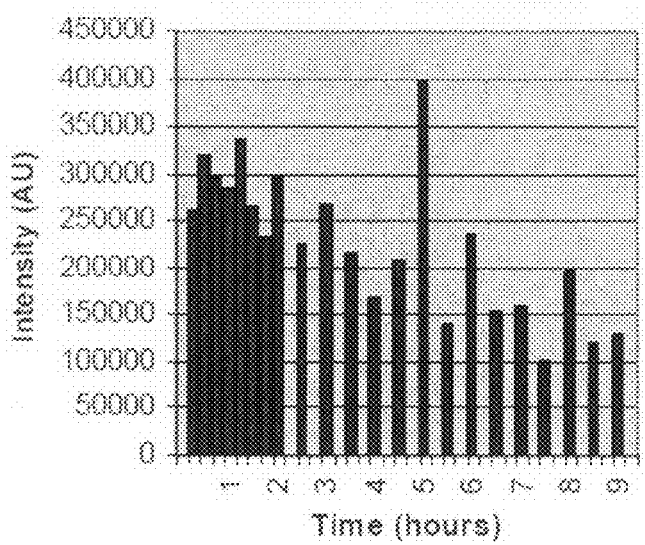
FIG. 10 shows the luminescence intensity response of a system of the invention as a function of time, upon exposure to peroxide vapor after (a) 1 day, (b) 2 days, and (c) 3 days.
Figure 10B:
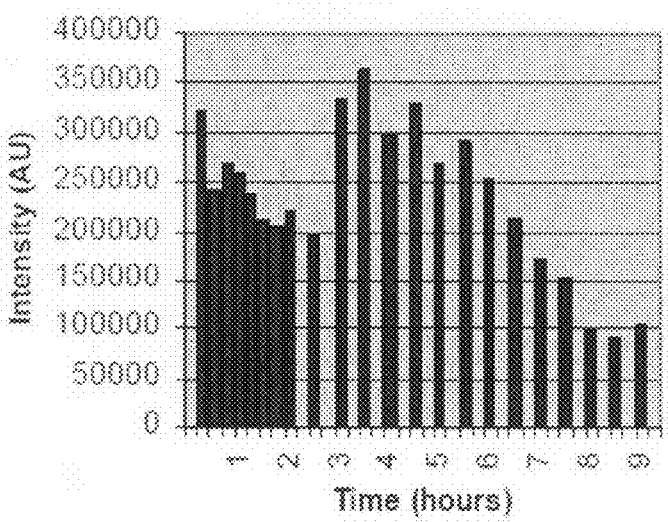
Figure 10C:
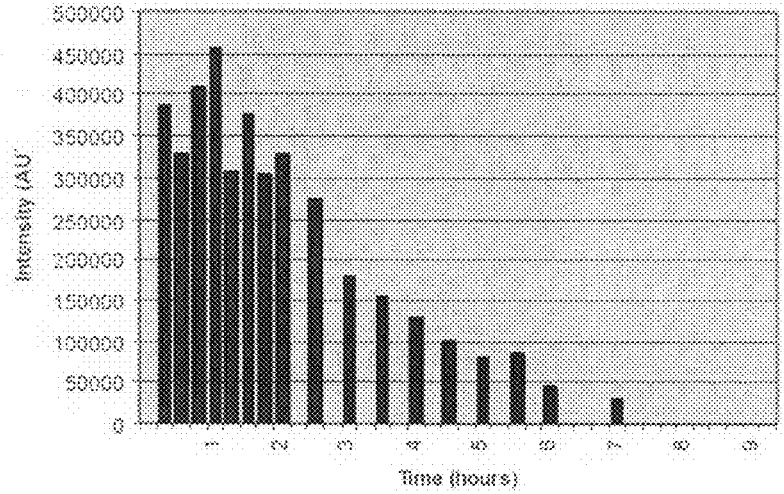

FIG. 10 shows the luminescence intensity of the material as a function of time upon exposure to exposure to the inside surface of a vial lid (inside surface) from a vial containing urea-peroxide crystals, after (a) 1 day, (b) 2 days, and (c) 3 days. As shown in FIGS. 10A-C, the capillary remained active towards peroxide vapor for around 2-3 days. However, increasing the volume of the DOTP-modified chemiluminescent solution to 225-250 microliters yielded improved shelf-life.

Figure 9:
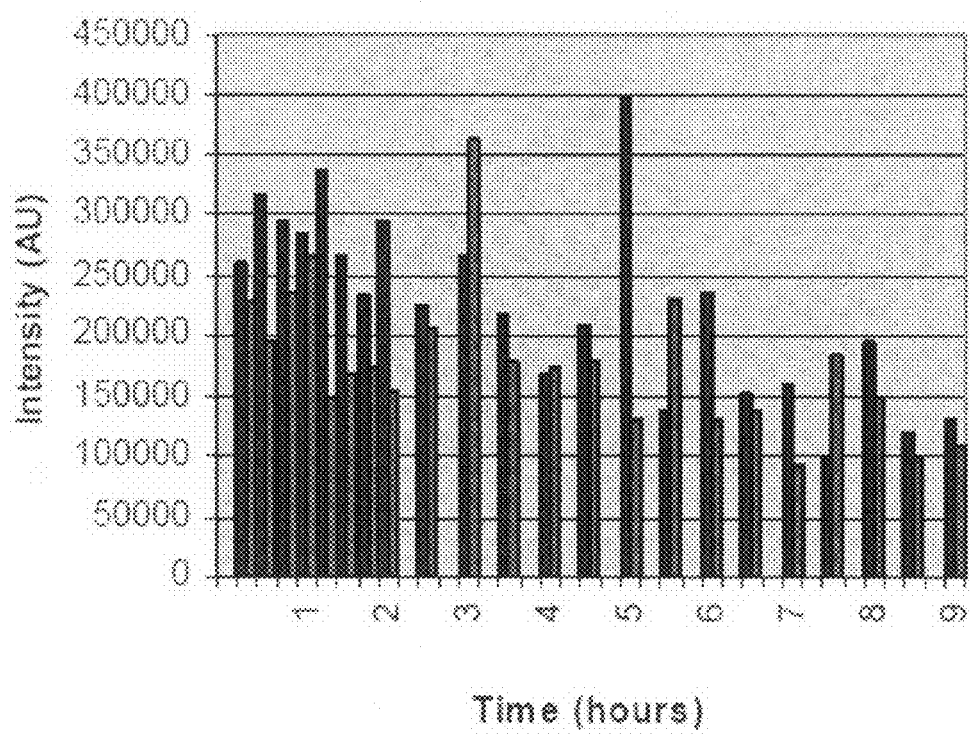
FIG. 9 shows the luminescence intensity of a chemiluminescent solution as a function of time one day after solvent exchange with dioctyl terephthalate (left columns), and, 23 days after solvent exchange with dioctyl terephthalate, with heating overnight on day 20 (right columns).

After ~3 weeks of dark storage in an oven-dried Schlenck flask at room temperature under an argon atmosphere, a small amount of clear, crystalline precipitate formed at the bottom of the flask containing the DOTP-modified solution. One day 20, the material was dissolved by heating the solution overnight at 90° C. in the absence of light, under argon atmosphere. FIG. 9 shows the luminescence intensity of the DOTP-modified solution as a function of time one day after the solvent exchange (left columns), and, 23 days after solvent exchange with heating overnight on day 20 (right columns). Testing of the system after 23 days yielded luminescence results comparable to freshly prepared solutions.

Example 3

Various formulations for the peroxide-reactive, chemiluminescent solution were investigated. Table 1 shows three solutions from which the formulations were made. The light-emitting material, TL-6-150, has the following structure,

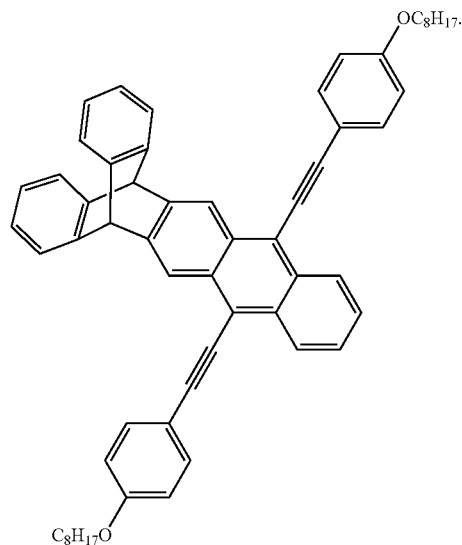

TABLE 1

Solutions comprising various components of systems of the invention.

| Solution | Components |
|---|---|
| 1 | 1.) bis(2,4,5-trichloro-6-carbopentoxyphenyl) oxalate (75 mg)<br>2.) 9,10-diphenyl anthracene (10 mg)<br>3.) DOTP(1 mL) |
| 2 | 1.) sodium salicylate (5 mg)<br>2.) di(propylene glycol) (1 mL) |
| 3 | 1.) bis(2,4,5-trichloro-6-carbopentoxyphenyl) oxalate (75 mg)<br>2.) TL-6-150(10 mg)<br>3.) DOTP (1 mL) |

TABLE 2

Chemiluminescent formulations having various compositions.

| Formulation | Solution 1 (microliters) | Solution 2 (microliters) | Solution 3 (microliters) | Ionic liquid (microliters) |
|---|---|---|---|---|
| A | 400 | 100 | — | — |
| B | 375 | — | — | 25 |
| C | 395 | — | — | 5 |
| D | — | 100 | 400 | — |
| E | — | — | 375 | 25 |
| F | — | — | 395 | 5 |

In solution, Formulations A-F displayed good luminescence response to a peroxide. FIG. 11A shows the average luminescence intensity response for formulations placed in frosted capillary, while FIG. 11B shows the average luminescence intensity response for formulations placed in frosted capillaries with frosted beads. When 50 microliter aliquots of the formulations were placed in capillaries with or without beads, only formulations B and E exhibited good responses towards 1-second exposure to a vial lid (inside surface) from a vial containing urea-peroxide crystals. However, the results indicated that the use of room temperature ionic liquids and/or iptycene-containing fluorescers may provide enhanced performance.

Example 4

Systems comprising an iptycene-containing light-emitting material were investigated.

Figure 12:
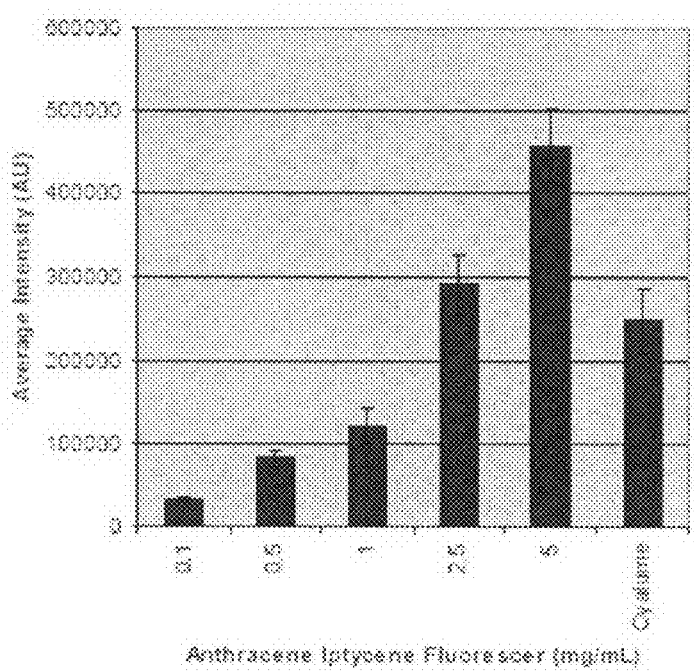
FIG. 12 shows the average luminescence intensity response of capillaries containing various chemiluminescent solutions, upon exposure to peroxide vapor.

Bis(2-Carbopentyloxy-3,5,6-trichlorophenyl) oxalate was obtained commercially and was recrystallized 3 times in hot isopropanol yielded a white crystalline solid that was pure by NMR. Stock solutions of the anthracene iptycene fluorescer, TL-6-150 (quantum yield=92% in THF), were prepared in DOTP, as listed in Table 3. Notably, TL-6-150 is also soluble at high concentrations (10 mg/mL) in DOTP. 100 µL of each stock solution was added to 50 mg of the recrystallized oxalate, and 50 µL of the solution was loaded into a frosted bead-filled capillary for testing in the Fido™ apparatus (65/55° C., 120 ccm) upon 1-second exposure to a vial lid (inside surface) from a vial containing urea-peroxide crystals. FIG. 12 shows the average luminescence intensity response of the capillaries containing the various solutions, with a Cyalume® test added for comparison.

Figure 13:
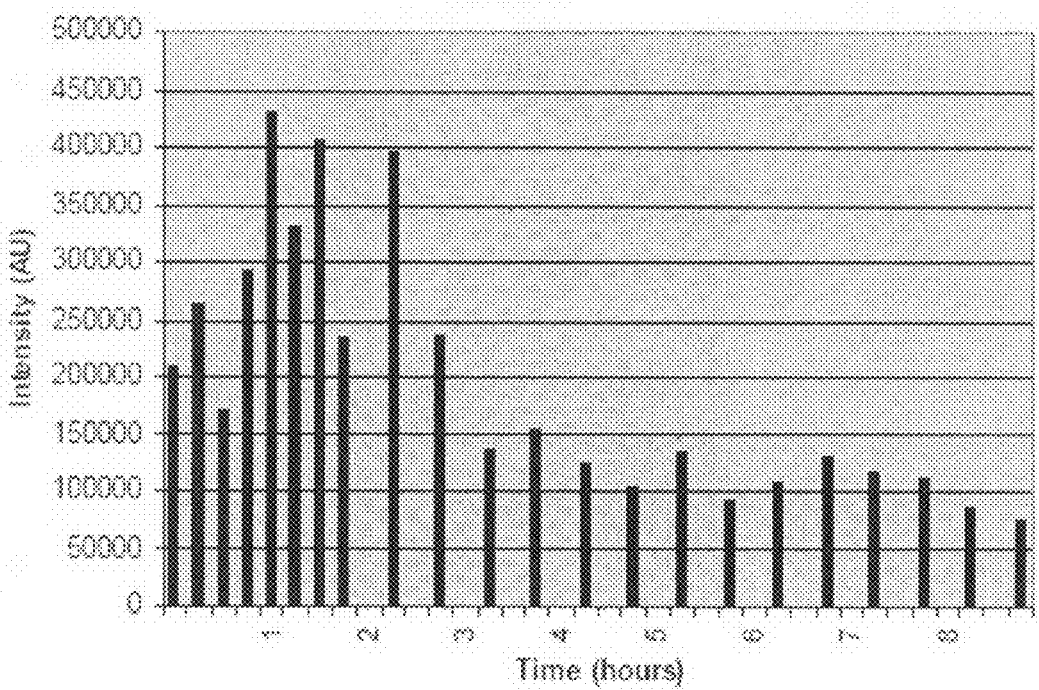
FIG. 13 shows the average luminescence intensity response for a frosted capillary containing frosted beads and 50 microliters of Solution E as a function of time, upon exposure to peroxide vapor.
Figure 14A:
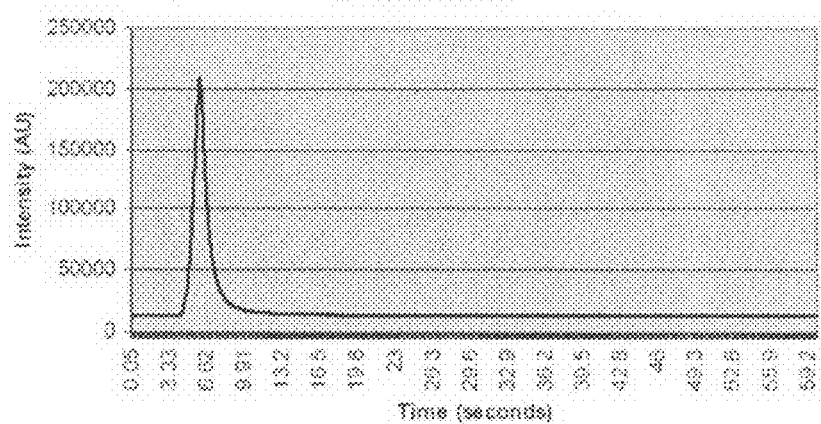
FIG. 14 shows the emission spectra for Solution E, upon exposure to peroxide vapor, at (a) 0.25 h, (b) 1.25 h, (c) 2.5 h, (d) 3.5 h, (e) 4.5 h, (f) 5.5 h, (g) 6.5 h, (h) 7.5 h, and (i) 9.0 h.
Figure 14B:
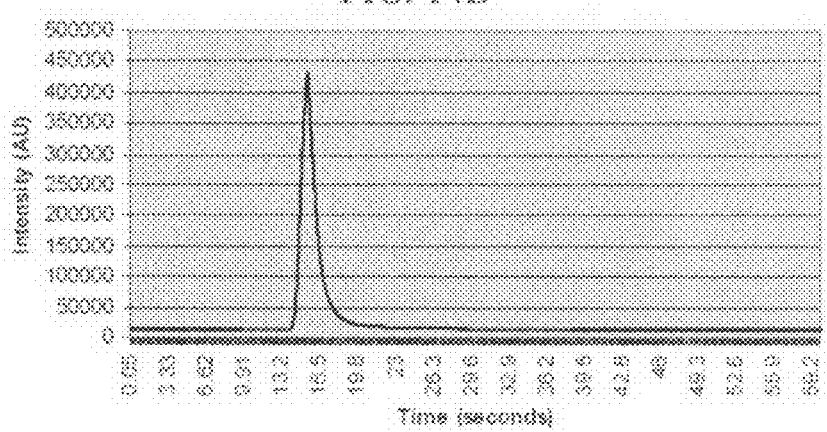
Figure 14C:
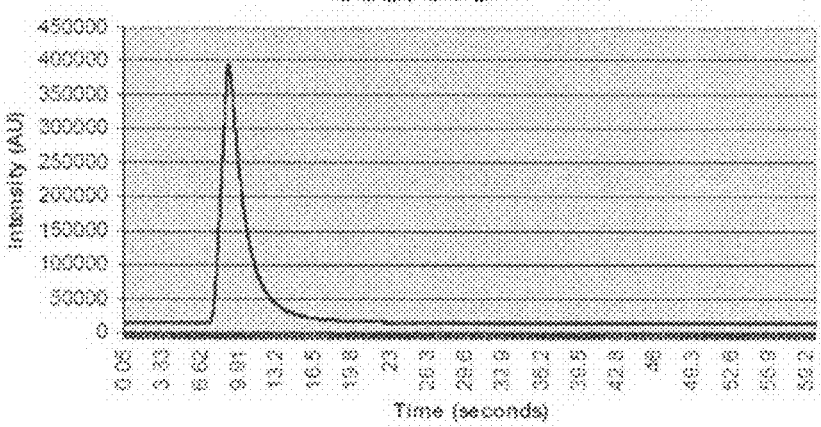
Figure 14D:
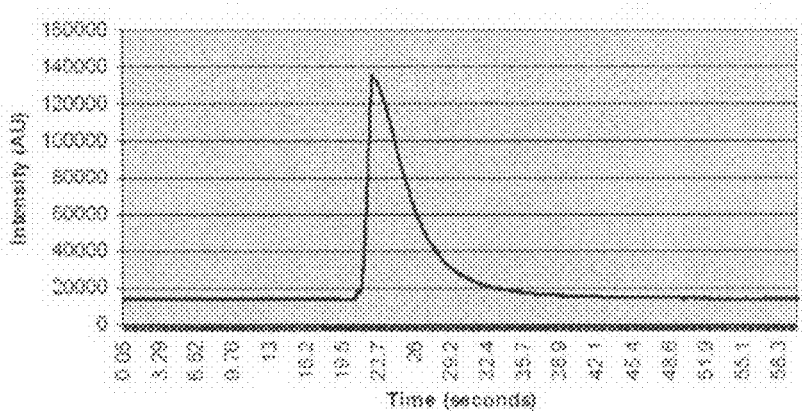
Figure 14E:
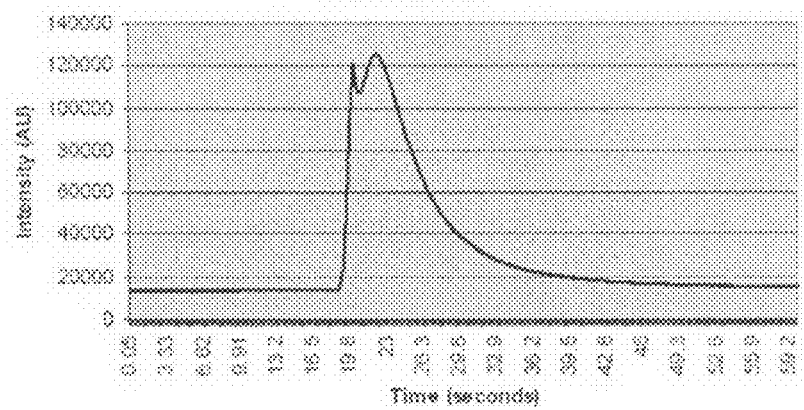
Figure 14F:
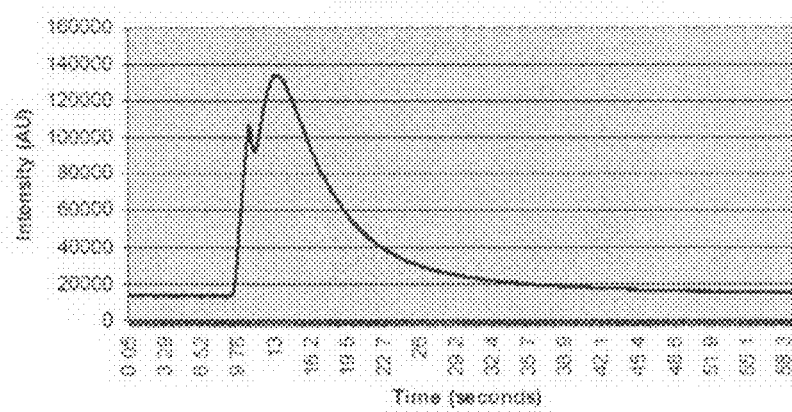
Figure 14G:
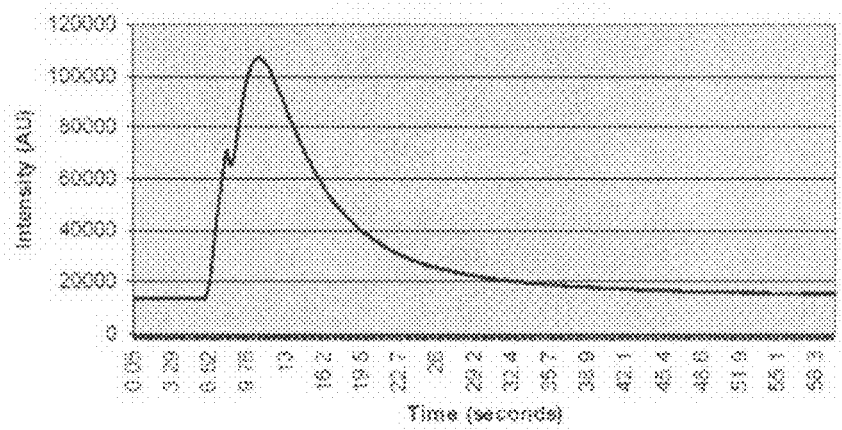
Figure 14H:
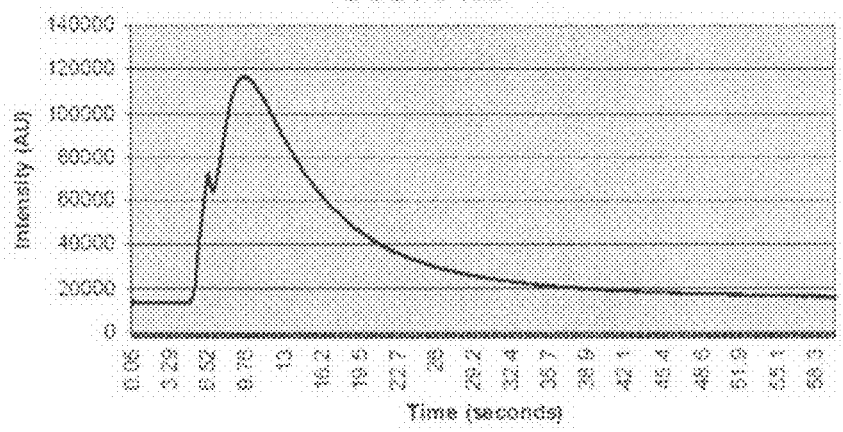
Figure 14I:
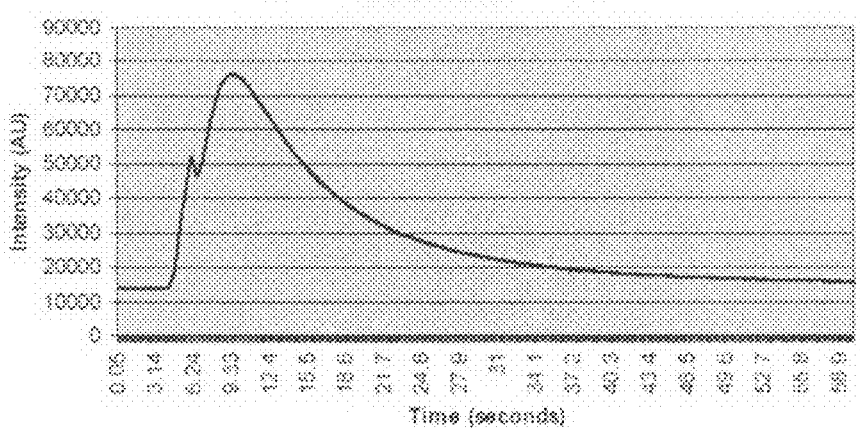

Continuous testing of the capillaries was also investigated. Upon exposure to the peroxide vapor, the luminescence emission of Solution E (5.0 mg/mL TL-6-150 in DOTP) was monitored over several hours. FIG. 13 shows the average luminescence intensity response for a frosted capillary containing frosted beads and 50 microliters of Solution E as a function of time. FIG. 14 shows the emission spectra for Solution E, upon exposure to peroxide vapor, at (a) 0.25 h, (b) 1.25 h, (c) 2.5 h, (d) 3.5 h, (e) 4.5 h, (f) 5.5 h, (g) 6.5 h, (h) 7.5 h, and (i) 9.0 h. Interestingly, the peak shape was found to change after ~3 hours of continuous testing.

TABLE 3

Solutions of TL-6-150 in DOTP.

| Solution | Amount of TL-6-150 in DOTP (mg/mL) |
| --- | --- |
| A | 0.1 |
| B | 0.5 |
| C | 1.0 |
| D | 2.5 |
| E | 5.0 |

Figure 15:
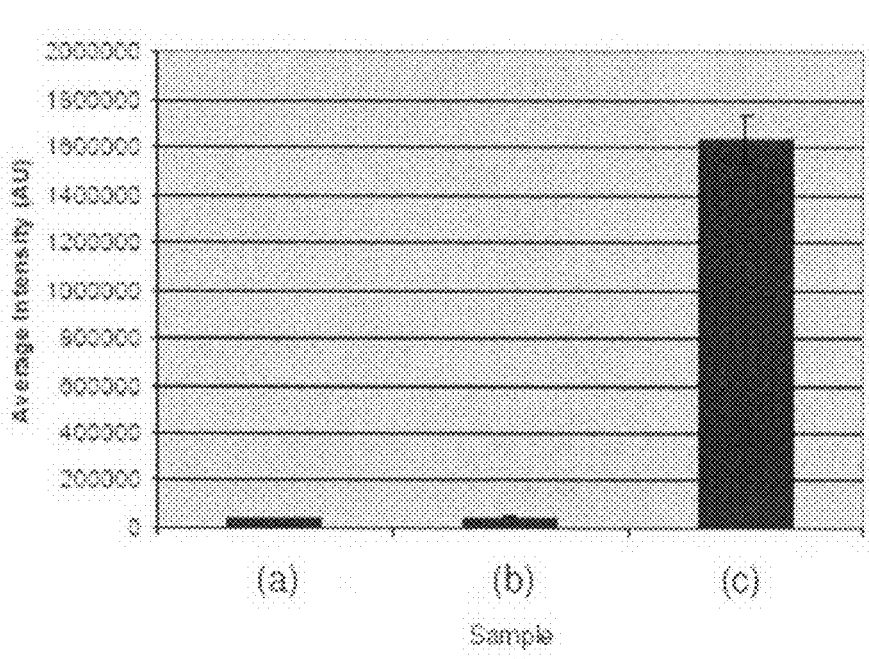
FIG. 15 shows the average luminescence intensity response of spin-coated samples containing dicyclohexyl phthalate, upon exposure to peroxide vapor.

To move towards "solid-state" materials for use as the chemiluminescent system in capillaries, toluene solutions of the a series of systems were spin-coated onto capillaries (without beads). FIG. 15 shows the average luminescence intensity response of the spin-coated samples of (a) a solution comprising a conjugated iptycene-containing poly(phenylene ethynylene and the recrystallized bis(2-carbopentyloxy-3,5,6-trichlorophenyl) oxalate; (b) a solution comprising TL-6-150 and the recrystallized oxalate; and (c) a solution comprising TL-6-150, the recrystallized oxalate, and phthalate dicyclohexyl phthalate, upon exposure to peroxide vapor. A dramatic increase in relative performance was observed upon addition of the solid-state phthalate, dicyclohexyl phthalate.

Example 5

Figure 16:
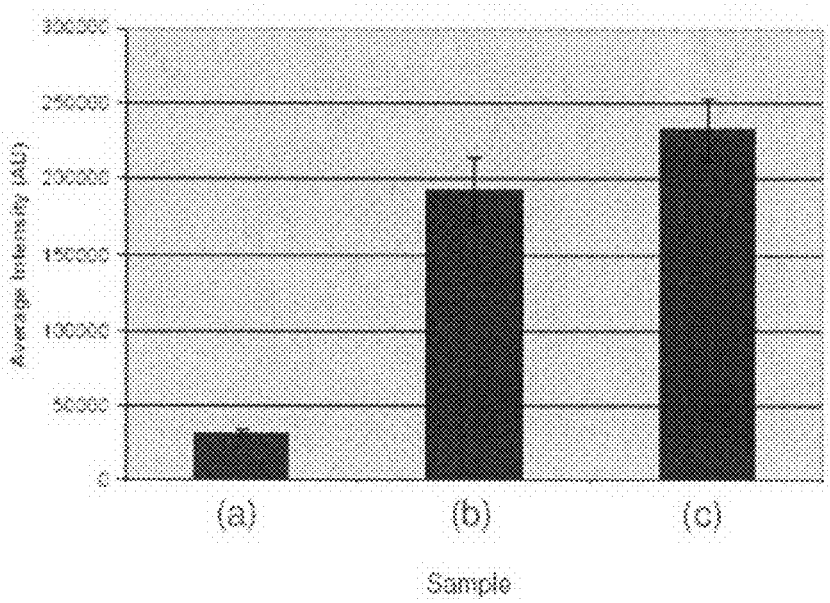
FIG. 16 shows the average luminescence intensity response of capillaries containing (a) an iptycene-containing poly(phenylene ethynylene), (b) 9,10-bis(phenyl-ethynyl)-anthracene (BPEA), and (c) TL-6-150, upon exposure to peroxide vapor.
Figure 17A:
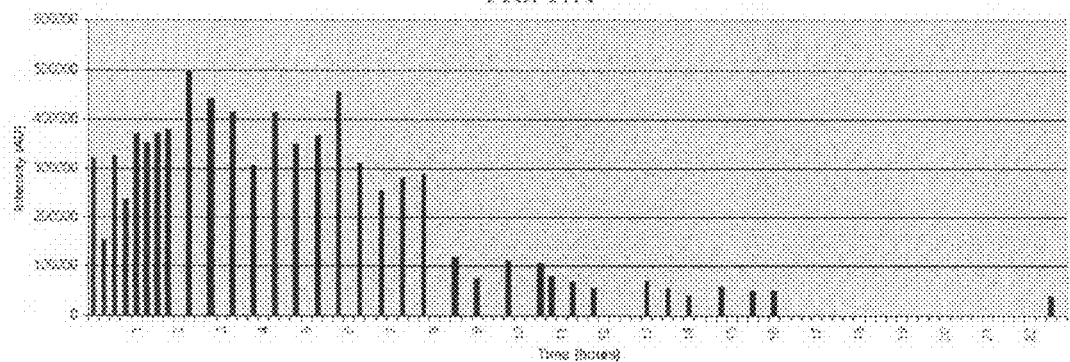
FIG. 17 shows the luminescence intensity response of capillaries as a function of time upon exposure peroxide vapor for solutions (a) I, (b) II, (c) III, (d) IV, (e) V, and (f) VI.
Figure 17B:
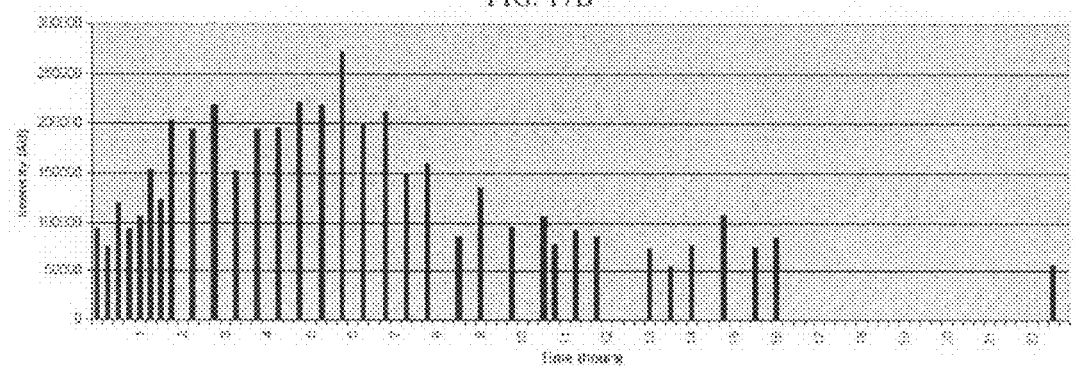
Figure 17C:
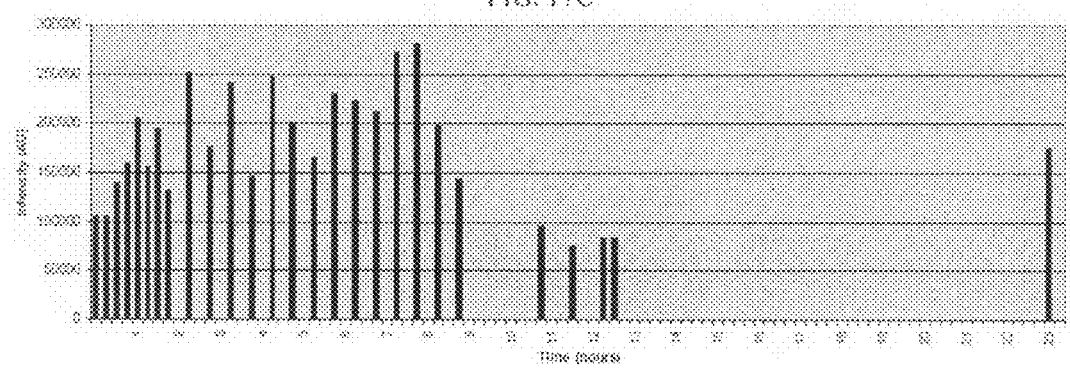
Figure 17D:
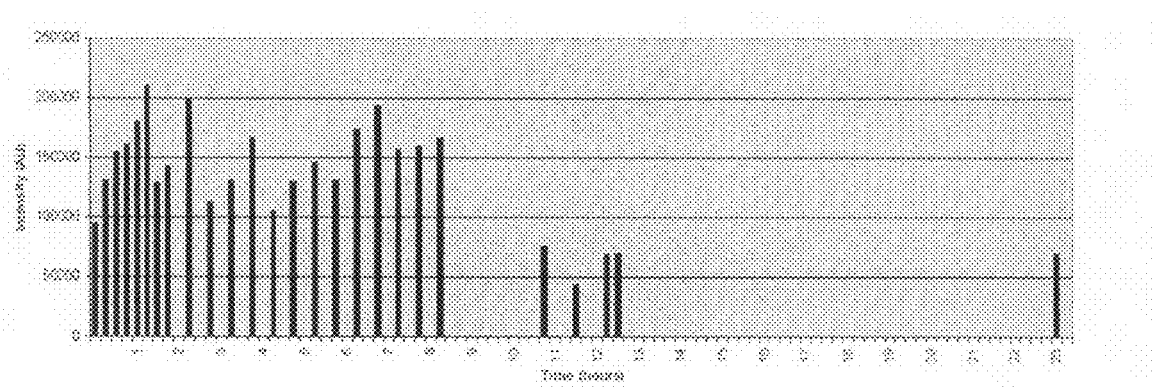
Figure 17E:
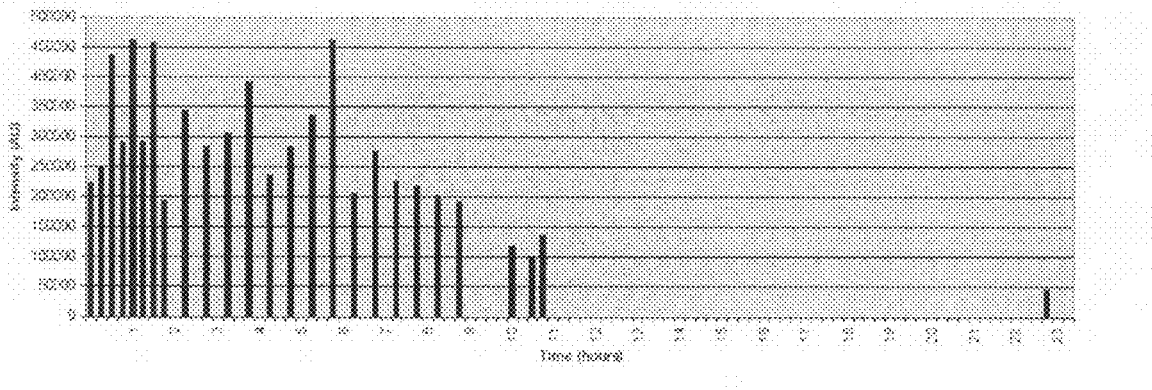
Figure 17F:
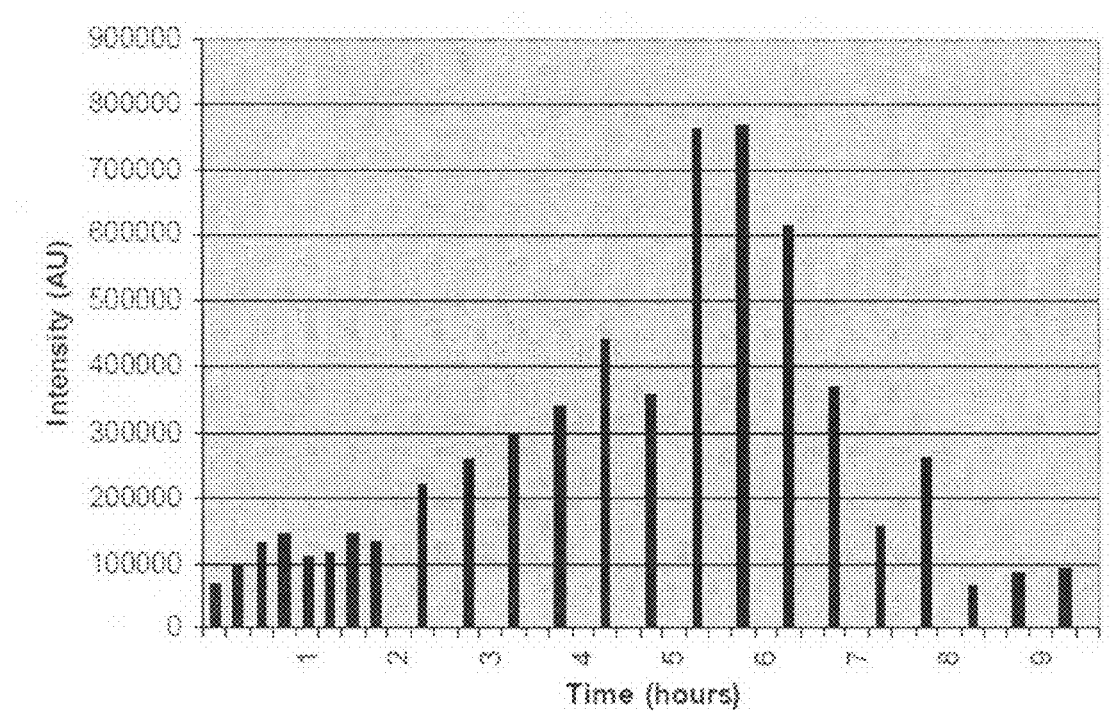

Based on the formulation studies described in Example 4, formulations comprising the following components were formed and evaluated for their luminescence response to peroxide vapor: 100 µL of a light-emitting material (selected from TL-6-150, an iptycene-containing poly(phenylene ethynylene, and 9,10-bis(phenylethynyl)anthracene) (5 mg/mL in toluene), 50 mg of recrystallized bis(2-carbopentyloxy-3,5,6-trichlorophenyl) oxalate, and 100 mg of dicyclohexyl phthalate. 50 µL of the resulting solutions was loaded onto a frosted bead-filled capillary, and was placed under high vacuum for 30 minutes to removed the volatile solvent, toluene. The resulting capillaries were tested in the Fido™ apparatus (65/65° C., 120 ccm) upon 1-second exposure to a vial lid (inside surface) from a vial containing urea-peroxide crystals. FIG. 16 shows the average luminescence intensity response of the capillaries containing (a) an iptycene-containing poly(phenylene ethynylene, (b) 9,10-bis(phenyl-ethynyl)-anthracene (BPEA), and (c) TL-6-150. As shown in FIG. 16, TL-6-150 and BPEA performed equally well, with the conjugated polymer exhibited lower response. Notably, the molecular weight of TL-6-150 (MW=810.10) is about double the molecular weight of BPEA (MW=378.48)

Additionally, the working lifetimes of the various formulations were also compared using the solutions listed in Table 4. In these solutions, bis(2-carbopentyloxy-3,5,6-trichlorophenyl) oxalate was recrystallized as described herein. Capillaries containing solutions I-VI were prepared by loading 50 µL of each solution into a frosted bead-filled capillary, and was placed under high vacuum for 30 minutes to removed the volatile solvent, toluene. The resulting capillaries were tested in the Fido™ apparatus (65/65° C., 120 ccm) upon 1-second exposure to a vial lid (inside surface) from a vial containing urea-peroxide crystals, There was no need to clean the optics of the Fido™ apparatus during this study. FIG. 17 shows the luminescence intensity response of the capillaries as a function of time upon exposure to a vial lid (inside surface) for solutions (a) I, (b) II, (c) III, (d) IV, (e) V, and (f) VI. Also, the shape and intensity of the emission peaks were altered after 8 hours, often resulting in a broadening of the peak and/or an increase in luminescence intensity.

TABLE 4

Solutions used to study working lifetime of systems of the invention.

Solution Components

| | |
| --- | --- |
| I | 1.) 100 µL of TL-6-150 (5 mg/mL in toluene) |
| | 2.) 50 mg bis(2-carbopentyloxy-3,5,6-trichlorophenyl) oxalate |
| | 3.) 100 mg of dicyclohexyl phthalate |
| II | 1.) 100 µL of TL-6-150 (5 mg/mL in toluene) |
| | 2.) 100 mg bis(2-carbopentyloxy-3,5,6-trichlorophenyl) oxalate |
| | 3.) 100 mg of dicyclohexyl phthalate |
| III | 1.) 50 µL of TL-6-150 (5 mg/mL in toluene) |
| | 2.) 50 µL toluene |
| | 3.) 50 mg bis(2-carbopentyloxy-3,5,6-trichlorophenyl) oxalate |
| | 4.) 100 mg of dicyclohexyl phthalate |
| IV | 1.) 100 µL of TL-6-150 (5 mg/mL in toluene) |
| | 2.) 50 mg bis(2-carbopentyloxy-3,5,6-trichlorophenyl) oxalate |
| | 3.) 200 mg of dicyclohexyl phthalate |
| V | 1.) 100 µL of BPEA (5 mg/mL in toluene) |
| | 2.) 50 mg bis(2-carbopentyloxy-3,5,6-trichlorophenyl) oxalate |
| | 3.) 100 mg of dicyclohexyl phthalate |
| VI | 1.) 50 µL of Cyalume ® solution (control) |

Example 6

The effect of capillary morphology, bead size, and surface chemistry on overall device performance was investigated.

Figure 18:
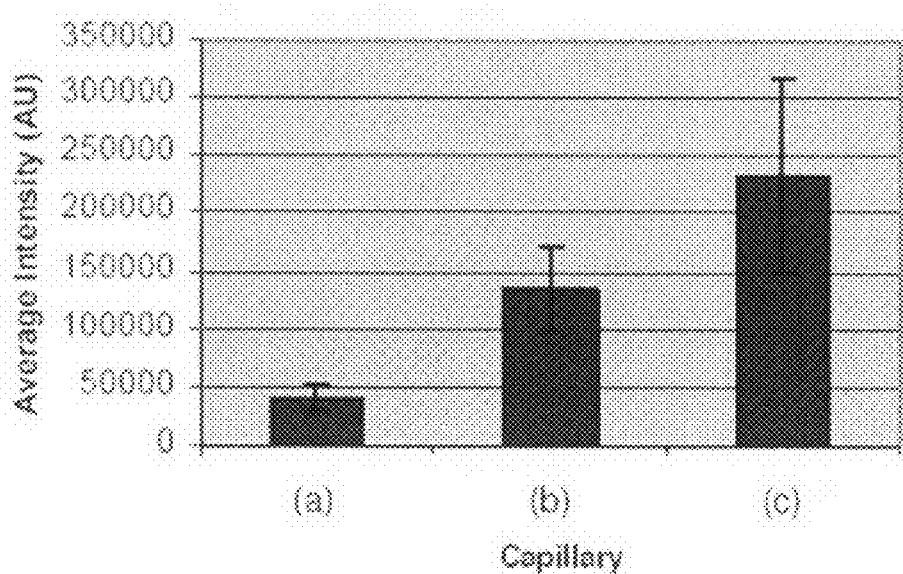
FIG. 18 shows the average luminescence intensity response for (a) capillaries with "opaque" ends (mechanically cut), (b) capillaries with clear but slightly rounded ends (mechanically cut, fire polished), and (c) capillaries with flat, clear ends (manually cut), upon exposure to peroxide vapor.

Capillaries having varied morphologies were studied with regard to efficiency of signal collection. Typically, the capillaries used are frosted, bead-filled capillaries with fire polished (e.g., rounded) ends. The capillaries were purchased commercially. In this study, various frosted capillaries were mechanically cut using a table top wet saw, or were manually scored and snapped. In some cases, the capillary was fire polished. The resulting capillaries were then filled with glass beads (2 mm, frosted/silanized), followed by a chemiluminescent solution (50 μL). FIG. 18 shows the average luminescence intensity response for (a) capillaries with "opaque" ends (mechanically cut), (b) capillaries with clear but slightly rounded ends (mechanically cut, fire polished), and (c) capillaries with flat, clear ends (manually cut), upon exposure to peroxide vapor. As shown in FIG. 18, the capillaries prepared by manual scoring and snapping yielded better signals than capillaries mechanically cut and fire polished.

Figure 19:
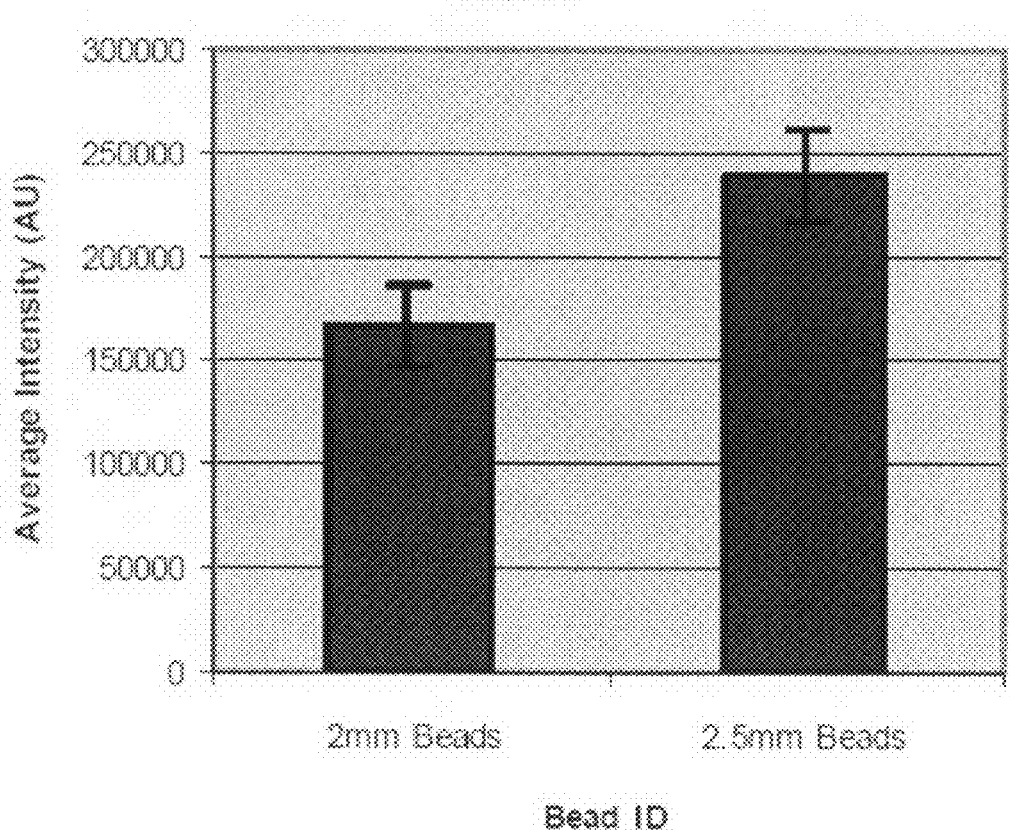
FIG. 19 shows the average luminescence intensity response for capillaries filled with 2.0 mm beads and 2.5 mm beads, upon exposure to peroxide vapor.

Different bead sizes were then tested to quantify the overall system performance as a function of bead size. Various glass beads (0.5, 1.0, 2.0, and 2.5 mm) were frosted, loaded into capillaries (frosted), and filled with chemiluminescent solution (50 μL). The resulting capillaries were then filled with glass beads (2 mm, frosted/silanized), followed by a chemiluminescent solution (50 μL). FIG. 19 shows the average luminescence intensity response for capillaries filled with 2.0 mm beads and 2.5 mm beads. As shown in FIG. 19, the capillaries filled with 2.5 mm beads exhibited enhanced luminescence, relative to the capillaries filled with 2.0 mm beads. Capillaries filled with 0.5 mm and 1.0 mm beads showed relatively lower response.

Figure 20A:
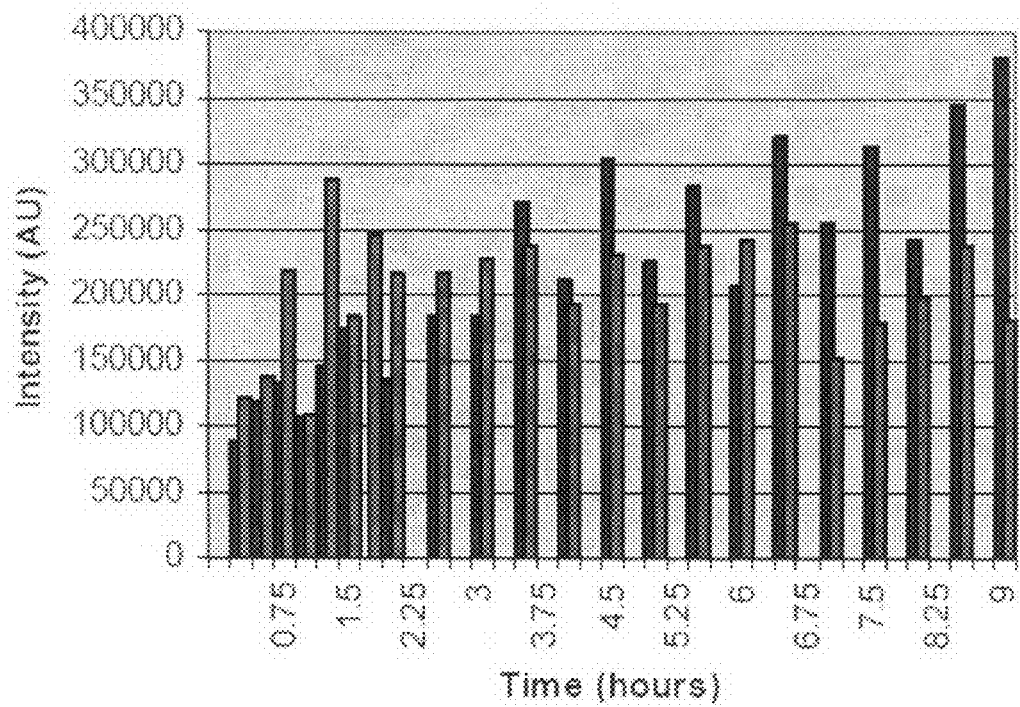
FIG. 20 shows the average luminescence intensity response for capillaries filled with (a) a Cyalume® solution and (b) a DOTP-modified solution, upon exposure to peroxide vapor as a function of time.
Figure 20B:
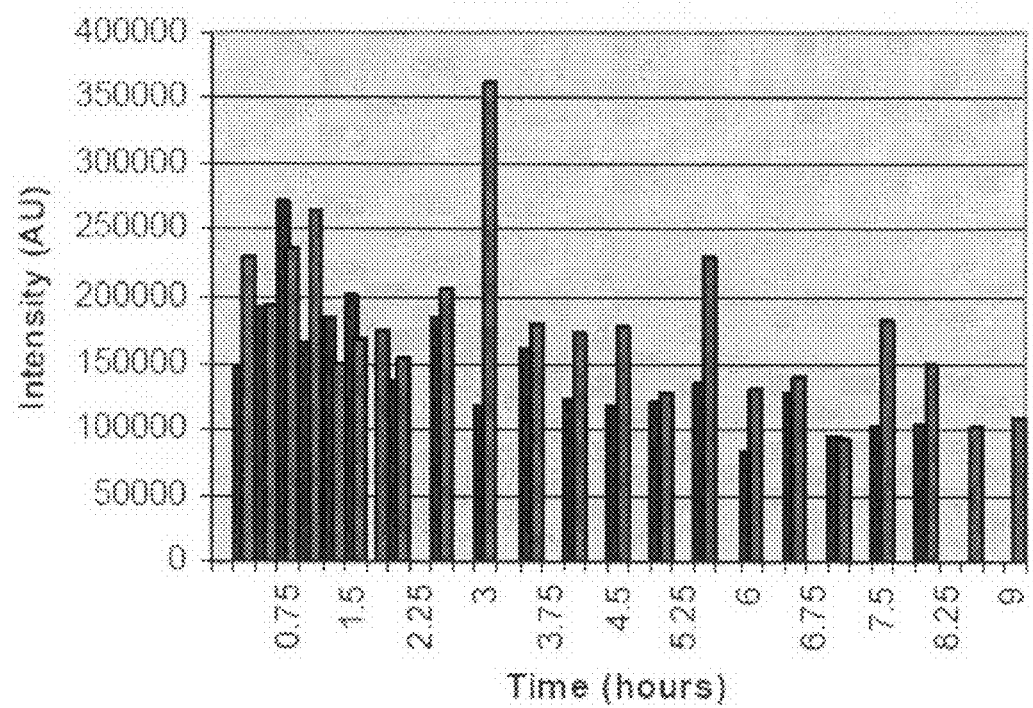

Next, the effect of bead size on overall working lifetimes was studied. Two capillaries were prepare, differing only in their chemiluminescent solution composition: First, a frosted/silanized glass capillary was filled with frosted/silanized 2.5 mm beads, followed by 50 μL of a freshly prepared chemiluminescent solution containing Cyalume®, as described in Example 1. Second, a frosted/silanized glass capillary was filled with frosted/silanized 2.5 mm beads, followed by 50 μL of a 24 day-old, DOTP-modified, chemiluminescent solution, as described in Example 2. FIG. 20 shows the average luminescence intensity response for capillaries filled with (a) the Cyalume® solution and (b) the DOTP-modified solution, upon exposure to peroxide vapor (via vial cap exposure, as described herein) as a function of time. As shown in FIGS. 20A-B, the capillary containing Cyalume® exhibited enhanced performance (most notably during the 4-9 hour testing window) relative to identical experiments performed using 2 mm beads, while the capillary containing the DOTP-modified solution exhibited approximately the same performance, relative to identical experiments with 2 mm beads. This may be due in part to the fact that an old DOTP-modified solution was used. In addition, condensation of the DOTP-modified solution was observed on the Fido™ optics, while no condensation of the Cyalume® solution was observed. This may be attributed to aerosolizing of the more viscous DOTP-modified material (120 ccm flowrate).

Figure 21:
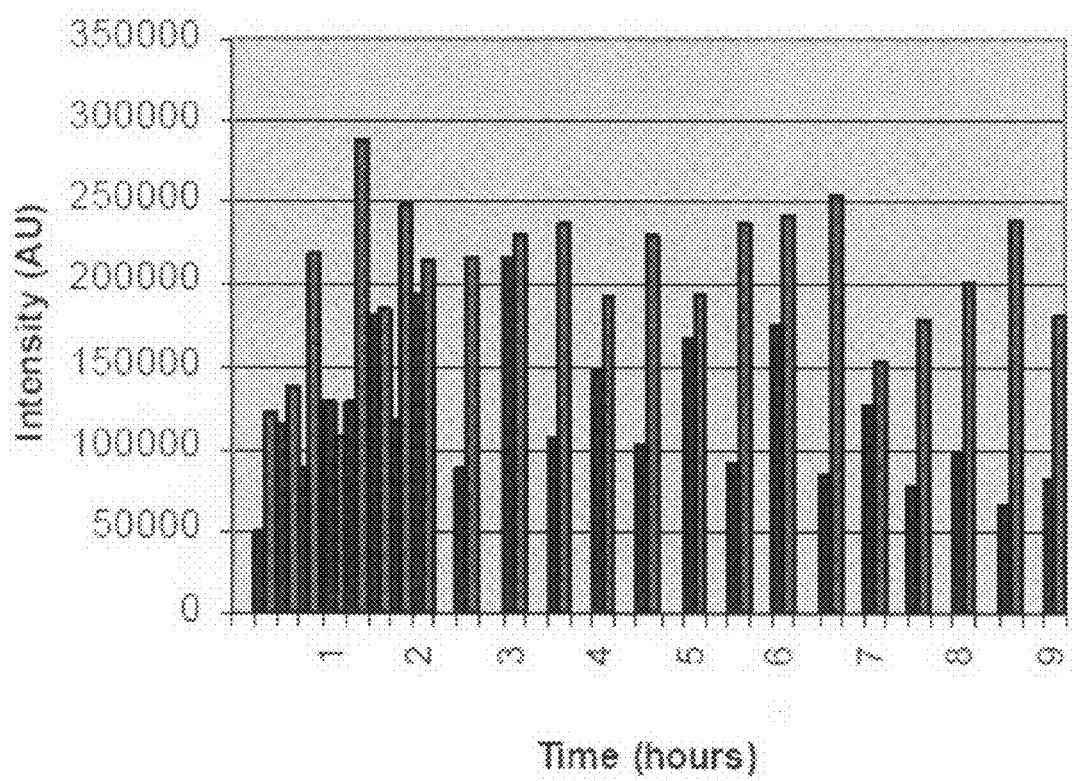
FIG. 21 shows the luminescence intensity response for unsilanized, bead-filled capillaries (left columns) and silanized, bead-filled capillaries (right columns), upon exposure to peroxide vapor as a function of time.

Finally, the surface chemistry of both the beads and capillary were studied. Silanization was performed to passivate the surfaces of both the beads and capillary, and the capillaries were filled with the same chemiluminescent system. FIG. 21 shows the luminescence intensity response for unsilanized, bead-filled capillaries (left columns) and silanized, bead-filled capillaries (right columns), upon exposure to peroxide vapor (via vial cap exposure, as described herein) as a function of time. As illustrated in FIG. 21, silanization of both the capillary and the beads significantly improved the overall working lifetime of the system when compared to an unsilanized capillary. Silanization of the capillary was shown to provide some benefit as well. This, in addition to pre-treatment of the glass with concentrated HCl to remove trace metal impurities, may yield significant benefits with regards to working lifetimes and/or shelf-life of the devices.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B", when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or"

as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of", when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed:

1. A system for determining a peroxide or a peroxide precursor, comprising:
a peroxide-reactive material, a light-emitting material, a support material, and, optionally, a catalyst, wherein the support material has a boiling point of at least 300° C. or greater, the peroxide-reactive material is bis(2-carbopentyloxy-3,5,6-trichlorophenyl)oxalate, and the light-emitting material is:

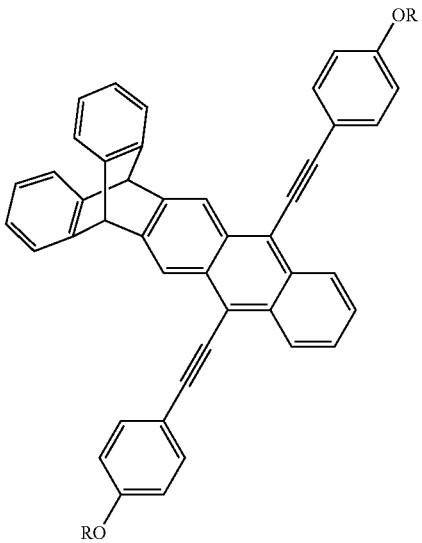

wherein R is alkyl, heteroalkyl, aryl or heteroaryl, the support material is dicyclohexyl phthalate, the catalyst, if present, is sodium salicylate, and wherein the peroxide-reactive material, light-emitting material, support material and catalyst are in liquid form.

2. The system of claim 1, further comprising a source of energy capable of converting an organic peroxide explosive to hydrogen peroxide.

3. The system of claim 1, wherein each of the peroxide-reactive material, light-emitting material, and catalyst, if present, is supported on the support material.

4. The system of claim 1, wherein the peroxide-reactive material, light-emitting material, and catalyst, if present, are combined in a homogenous mixture, the mixture supported on the support material.

5. The system of claim 1, wherein the peroxide-reactive material, light-emitting material, and catalyst, if present, are evenly dispersed within the support material.

6. The system of claim 1, wherein the peroxide-reactive material, light-emitting material, and catalyst, if present, are adsorbed onto the support material.

7. The system of claim 1, wherein, when combined, the peroxide-reactive material, light-emitting material, the support material, and catalyst, if present, form a solution.

8. The system of claim 1, wherein the catalyst enhances the ability of the system to emit light.

9. The system of claim 1, wherein the light-emitting material has an emission spectrum between 330-1200 nm.

10. The system of claim 1, wherein the light-emitting material is covalently bonded to the peroxide-reactive material.

11. The system of claim 1, wherein the light-emitting material is covalently bonded to the support material.

12. The system of claim 1, wherein R is octyl.

13. The system of claim 1, wherein the system exhibits chemiluminescence in the presence of a peroxide.

14. The system of claim 1, further comprising a material capable of converting a peroxide precursor to a peroxide.

15. The system of claim 14, wherein the material comprises an acid.

16. The system of claim 1, wherein, in the presence of a peroxide, the light-emitting material has a quantum yield of at least 50%.

17. A method for making a composition for determining a peroxide or a peroxide precursor, comprising:

forming a liquid mixture comprising a peroxide-reactive material, a light-emitting material, a support material or support material precursor, and, optionally, a catalyst, to produce a composition that is emissive in the presence of a peroxide, wherein the composition has a boiling point of at least 300° C. or greater, the peroxide-reactive material is bis(2-carbopentyloxy-3,5,6-trichlorophenyl)oxalate, and the light-emitting material is:

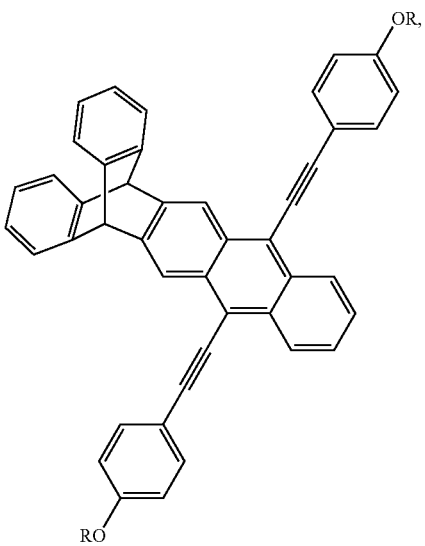

wherein R is alkyl, heteroalkyl, aryl or heteroaryl, the support material or precursor is dicyclohexyl phthalate and the catalyst, if present, is sodium salicylate.

18. The method of claim 17, further comprising:
solidifying the liquid mixture to produce a solid composition that is emissive in the presence of a peroxide.

19. The method of claim 17, wherein the emissive composition is chemiluminescent.

20. The method of claim 17, wherein forming the liquid mixture comprises dissolving or suspending the peroxide-reactive material, light-emitting material, support material or support material precursor, and catalyst, if present, in an auxiliary fluid.

21. The method of claim 20, wherein the auxiliary fluid is a solvent, and forming the liquid mixture comprises dissolving the peroxide-reactive material, light-emitting material, support material or support material precursor, and catalyst, if present, in the solvent.

22. The method of claim 21, wherein the solvent is ethylene glycol ethers, diethyl ether, diamyl ether, diphenyl ether, anisole, tetrahydrofuran, dioxane, ethyl acetate, propyl formate, amyl acetate, dimethyl phthalate, diethyl phthalate, dibutyl phthalate, dioctyl phthalate, methyl formate, triacetin, diethyl oxalate, dioctyl terphthalate, citric acid ester, methyl benzoate, ethyl benzoate, butyl benzoate, benzene, ethyl benzene, butyl benzene, toluene, xylene, chlorobenzene; o-dichlorobenzene, m-dichlorobenzene, chloroform, carbon tetrachloride, hexachloroethylene, tetrachlorotetrafluoropropane, or combinations thereof.

23. The method of claim 17, wherein the catalyst enhances the ability of the system to emit light.

24. The method of claim 17, wherein the peroxide-reactive material, the catalyst, and the light-emitting material are evenly dispersed within the support material.

25. The system of claim 17, further comprising a material of converting peroxid precursor to a peroxid.

26. A method for determining a peroxide, comprising:
exposing a composition comprising a peroxide-reactive material, a light-emitting material, a support material or support material precursor, and, optionally, a catalyst to a vapor suspected of containing a peroxide,
wherein the peroxide-reactive material is bis(2-carbopentyloxy-3,5,6-trichlorophenyl)oxalate, the light-emitting material is:

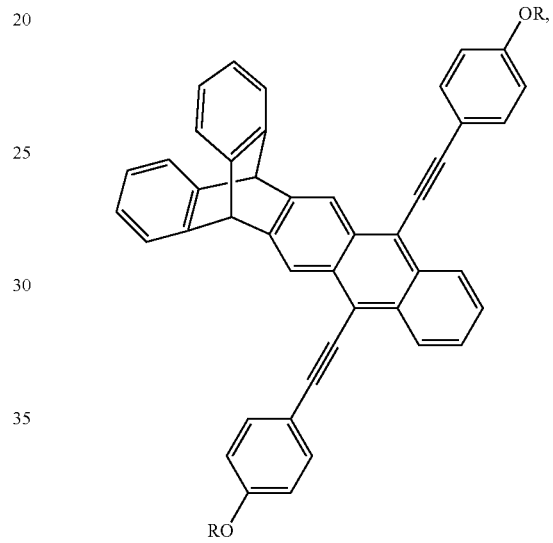

wherein R is alkyl, heteroalkyl, aryl or heteroaryl, the support material or precursor is dicyclohexyl phthalate and the catalyst, if present, is sodium salicylate, wherein the peroxide-reactive material, light-emitting material, support material and catalyst are in liquid form, and wherein the peroxide, if present, causes the composition to generate a determinable signal, wherein the composition has a boiling point of at least 300° C. or greater; and
determining the signal.

27. The method of claim 17, wherein the catalyst enhances the ability of the system to emit light.

28. The method of claim 26, wherein the signal is emission of light.

29. The method of claim 26, wherein the peroxide or peroxide precursor is an explosive.

30. The method of claim 29, wherein the explosive is triacteone triperoxide (TATP).

31. The method of claim 29, wherein the explosive is hexamethylene triperoxide diamine (HMTD).

* * * * *

UNITED STATES PATENT AND TRADEMARK OFFICE
CERTIFICATE OF CORRECTION

PATENT NO. : 7,799,573 B2
APPLICATION NO. : 11/784208
DATED : September 21, 2010
INVENTOR(S) : Robert Deans et al.

Page 1 of 1

It is certified that error appears in the above-identified patent and that said Letters Patent is hereby corrected as shown below:

On the title page: Item (73) should read: (73) Assignee: Nomadics, Inc., Stillwater, OK (US)

At column 31, claim 17, line 35, please change "alkyl" to --akyl--

At column 31, claim 17, line 35, please change "heteroaryl" to --heteraryl--

At column 32, claim 25, line 5, please insert at the end --capable--

At column 32, claim 25, line 6, please change "converting peroxid" to --converting a peroxide--

At column 32, claim 25, line 6, please change "precursor to a peroxid" to --precursor to a peroxide--

At column 32, claim 26, line 13, please change "a catalyst to" to --catalist, to--

At column 32, claim 26, line 42, please change "alkyl" to --akyl--

At column 32, claim 26, line 42, please change "heteroaryl" to --heteraryl--

At column 32, claim 27, line 51, please change "claim 17" to --claim 26--

Signed and Sealed this

Sixteenth Day of November, 2010

David J. Kappos
*Director of the United States Patent and Trademark Office*